United States Patent
Hu et al.

(10) Patent No.: US 11,033,237 B2
(45) Date of Patent: Jun. 15, 2021

(54) METHOD AND APPARATUS FOR PREDICTING A USE FOR A BLOOD TRANSFUSION

(71) Applicants: Fu-Ming Hu, Ellicott City, MD (US); Colin F. Mackenzie, Pasadena, MD (US); Shiming Yang, Halethorpe, MD (US); Konstantinos Kalpakis, Bethesda, MD (US)

(72) Inventors: Fu-Ming Hu, Ellicott City, MD (US); Colin F. Mackenzie, Pasadena, MD (US); Shiming Yang, Halethorpe, MD (US); Konstantinos Kalpakis, Bethesda, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 193 days.

(21) Appl. No.: 16/099,789

(22) PCT Filed: May 11, 2017

(86) PCT No.: PCT/US2017/032169
§ 371 (c)(1),
(2) Date: Nov. 8, 2018

(87) PCT Pub. No.: WO2017/197120
PCT Pub. Date: Nov. 16, 2017

(65) Prior Publication Data
US 2019/0133534 A1   May 9, 2019

Related U.S. Application Data

(60) Provisional application No. 62/334,750, filed on May 11, 2016.

(51) Int. Cl.
*A61B 5/316* (2021.01)
*A61B 5/00* (2006.01)
(Continued)

(52) U.S. Cl.
CPC .............. *A61B 5/7257* (2013.01); *A61B 5/00* (2013.01); *A61B 5/02042* (2013.01);
(Continued)

(58) Field of Classification Search
CPC ............ A61B 5/02042; A61B 5/02416; A61B 5/04014; A61B 5/7257; A61B 5/7264
See application file for complete search history.

(56) References Cited

U.S. PATENT DOCUMENTS

| | | | |
|---|---|---|---|
| 2007/0032732 A1 | 2/2007 | Shelley et al. | |
| 2010/0298675 A1 | 11/2010 | Al-Ali et al. | |
| 2013/0172702 A1* | 7/2013 | Shelley .................. | A61B 5/746 600/324 |

FOREIGN PATENT DOCUMENTS

| | | | | |
|---|---|---|---|---|
| WO | 2015023708 A1 | 2/2015 | | |
| WO | 2015023708 A9 | 2/2015 | | |
| WO | WO 2015/023708 A1 * | 2/2015 | ......... | A61B 5/02042 |

OTHER PUBLICATIONS

Extended Search Report for European Patent Application No. 17796845.0 dated Nov. 12, 2019, pp. 1-9.
(Continued)

*Primary Examiner* — Eric D. Bertram
(74) *Attorney, Agent, or Firm* — Wolter Van Dyke Davis, PLLC; Eugene J. Molinelli; Cian O'Brien

(57) ABSTRACT

A method is provided for predicting that a caregiver will order a blood transfusion during a treatment. The method includes obtaining, on a processor, first data that indicates values for one or more parameters of a characteristic of a peak of a Fourier transform of a continuous photoplethysmographic (PPG) waveform or a continuous electrocardiogram (ECG) waveform or both collected during the treatment. The method further includes applying, on the processor, coefficients to the values for the one or more parameters. The method further includes determining, on the
(Continued)

processor, second data that indicates a prediction that the caregiver will order the blood transfusion during the treatment based on applying the coefficients to the values. The method further includes presenting on a display device output data based on the second data. An apparatus is also provided for predicting that the caregiver will order the blood transfusion during the treatment.

28 Claims, 16 Drawing Sheets

(51) Int. Cl.
      *A61B 5/02*       (2006.01)
      *A61B 5/024*      (2006.01)
      *A61B 5/0295*     (2006.01)
      *A61B 5/1455*     (2006.01)
      *G16H 50/30*      (2018.01)

(52) U.S. Cl.
      CPC ........ *A61B 5/02416* (2013.01); *A61B 5/7264* (2013.01); *A61B 5/0295* (2013.01); *A61B 5/1455* (2013.01); *A61B 5/316* (2021.01); *G16H 50/30* (2018.01)

(56) References Cited

OTHER PUBLICATIONS

International Search Report and Written Opinion, International Patent Application No. PCT/US2017/32169, dated Sep. 28, 2017, pp. 1-9.

Hu et al., Reliable Collection of Real-time Patient Physiologic Data from Less Reliable Networks: a "monitor of monitors" system (MoMs), Journal of Medical Systems, 2017, pp. 1-8, vol. 41.

Galvagno et al., Accuracy of continuous noninvasive hemoglobin monitoring for the prediction of blood transfusions in trauma patients, J Clin Monit Comput, 2015, pp. 815-821, vol. 29.

MacKenzie et al., Comparison of Decision-Assist and clinical judgment of experts for prediction of lifesaving interventions, Shock, 2015, pp. 238-243, vol. 43.

MacKenzie et al, Automated prediction of early blood transfusion and morality in trauma patients, J Trauma Acute Care Surg, 2014, pp. 1379-1385, vol. 76.

Shackelford et al., Predicting blood transfusion using automated analysis of pulse oximetry signals and laboratory values, J Trauma Acute Care Surg, 2015, pp. S175-S180, vol. 79.

\* cited by examiner

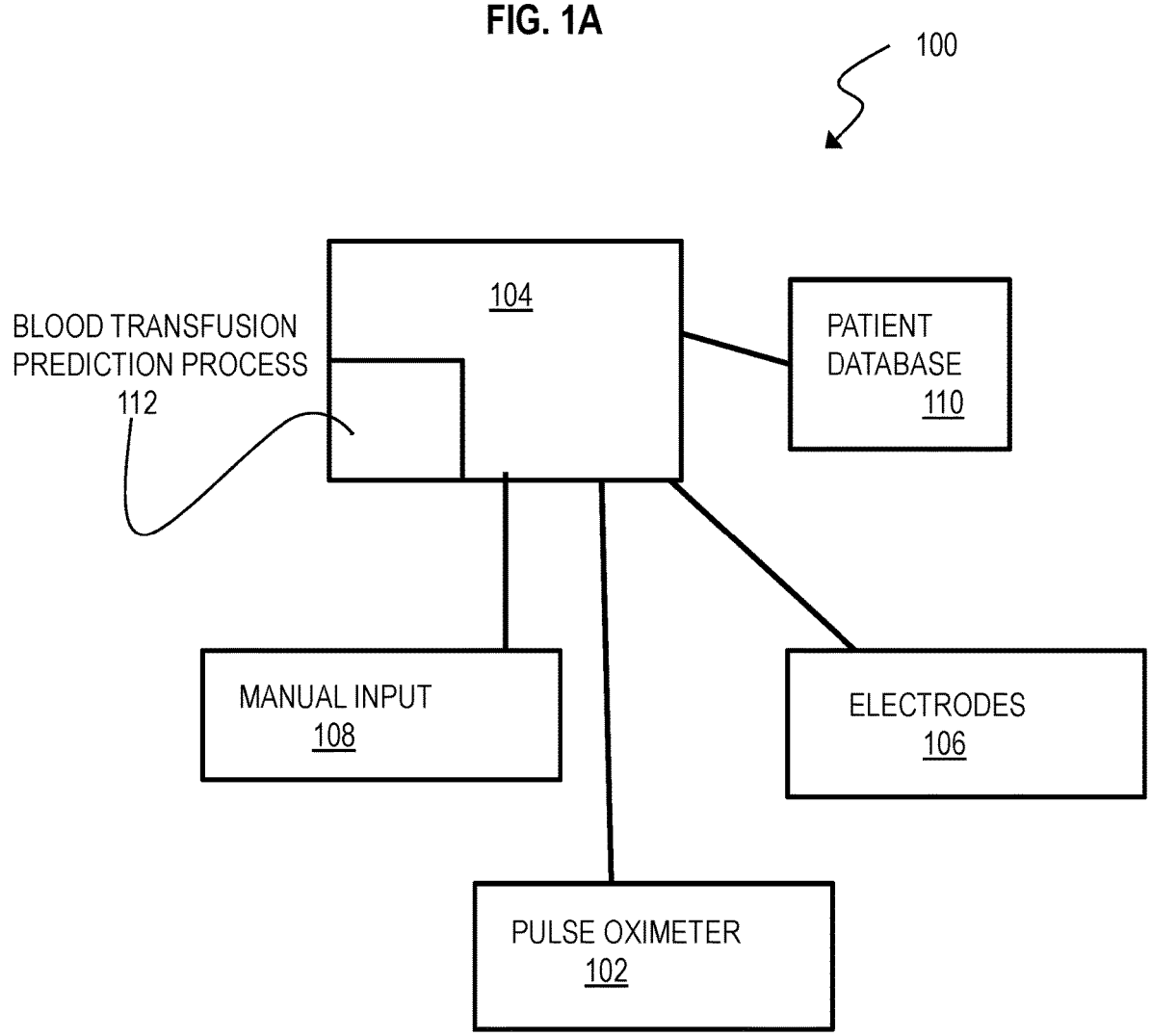

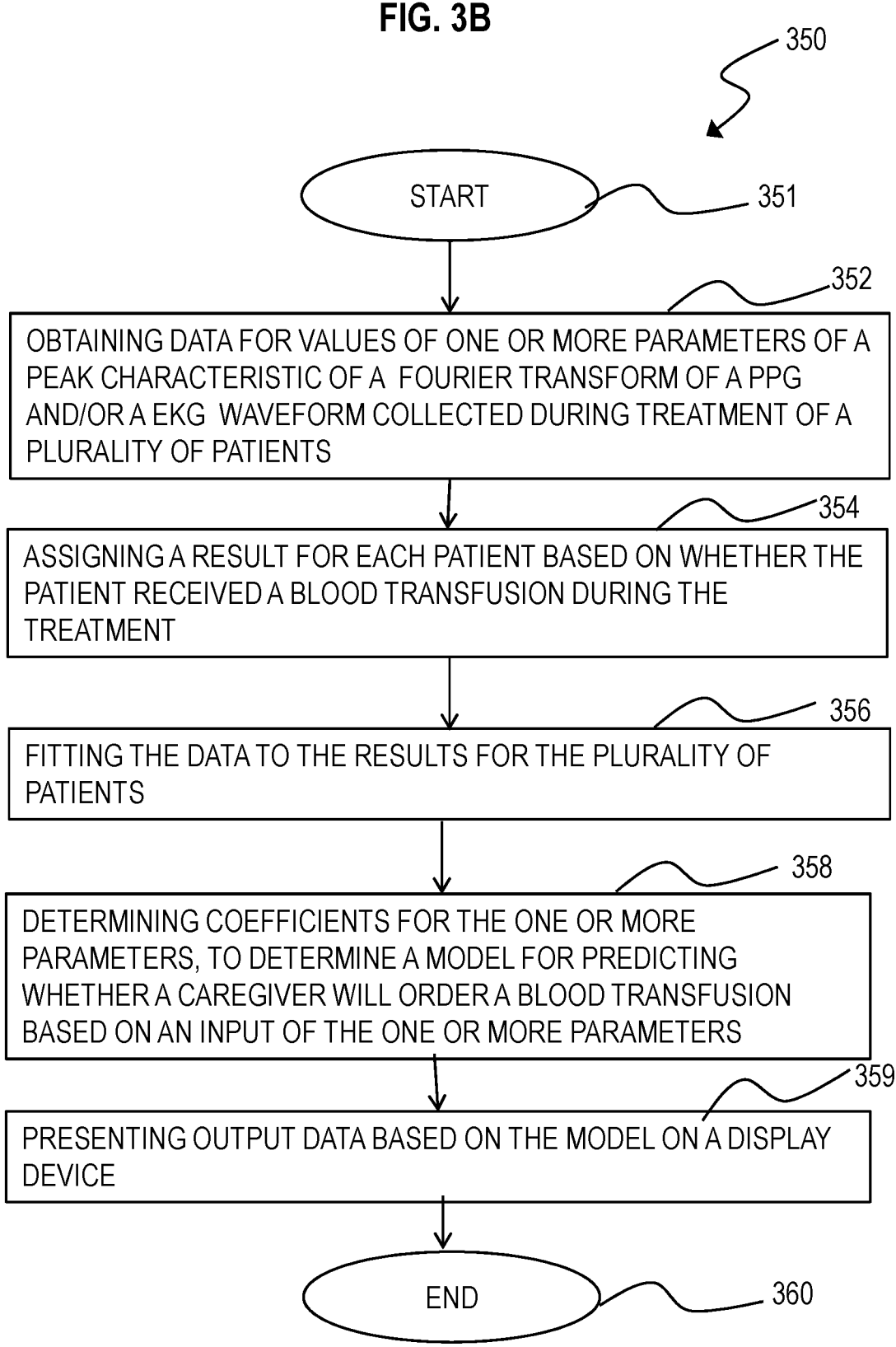

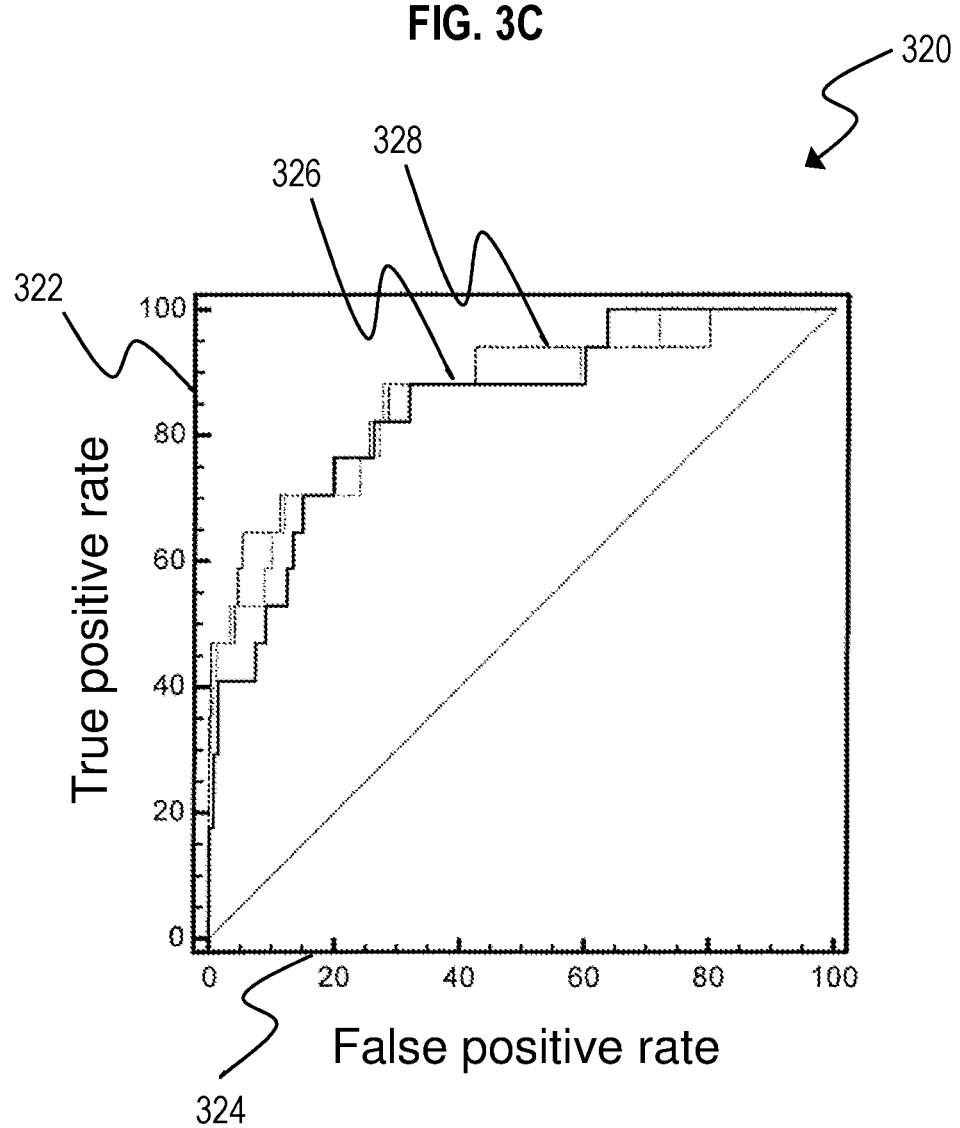

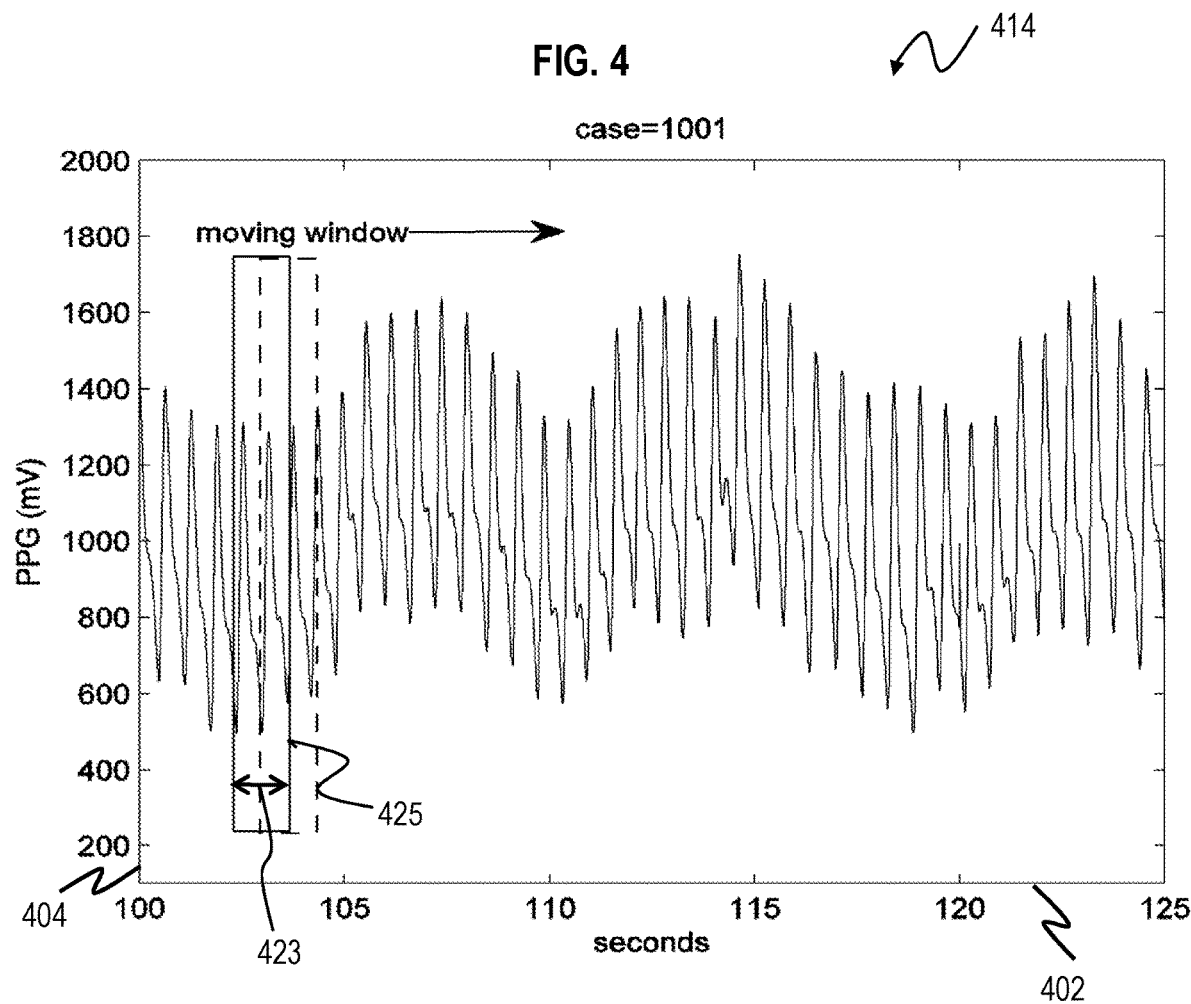

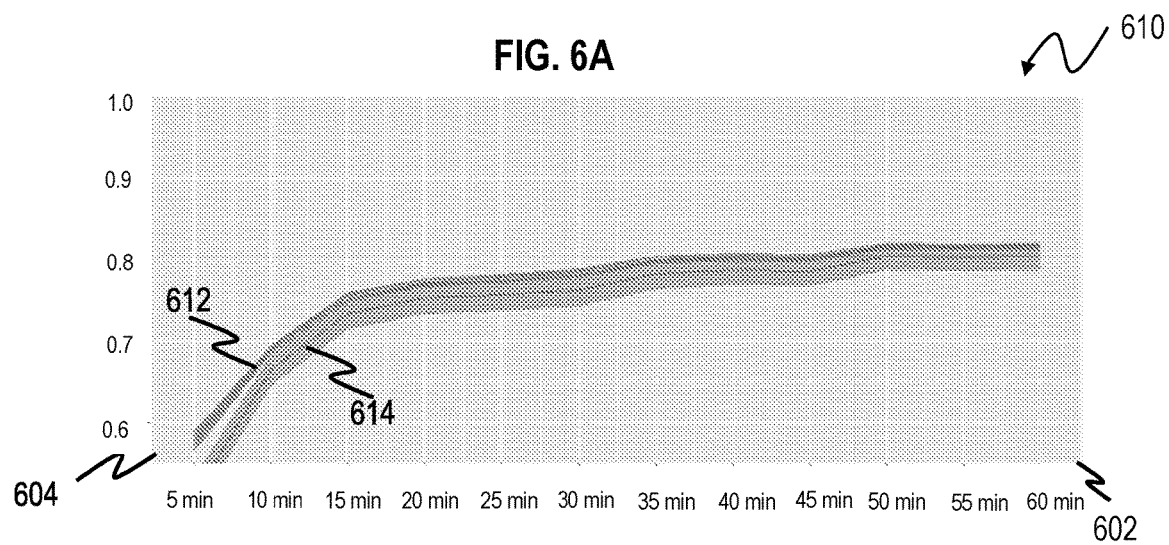
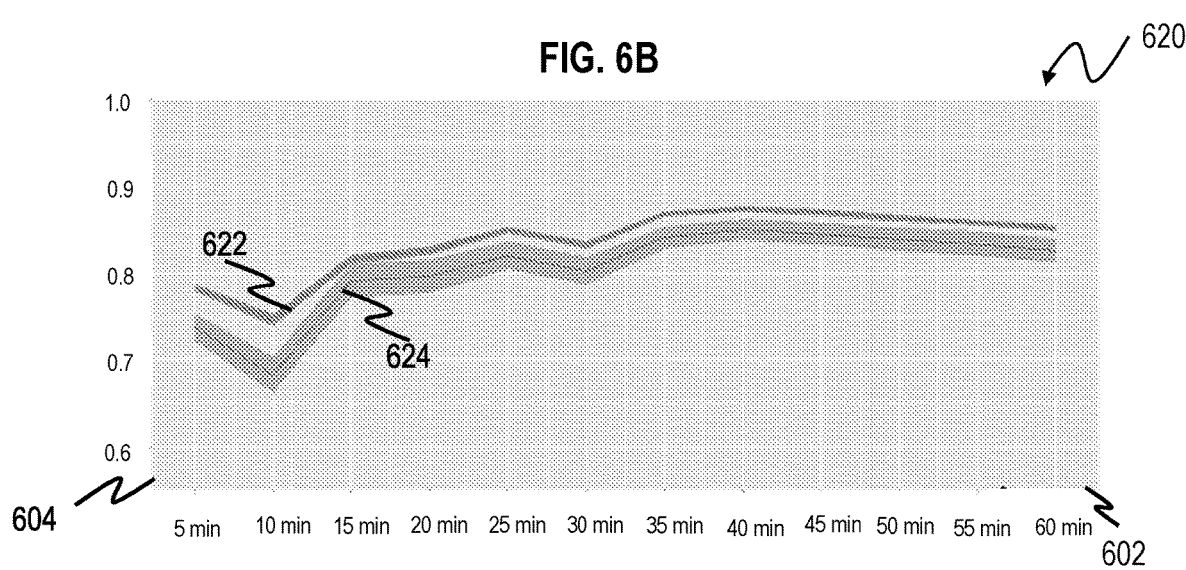
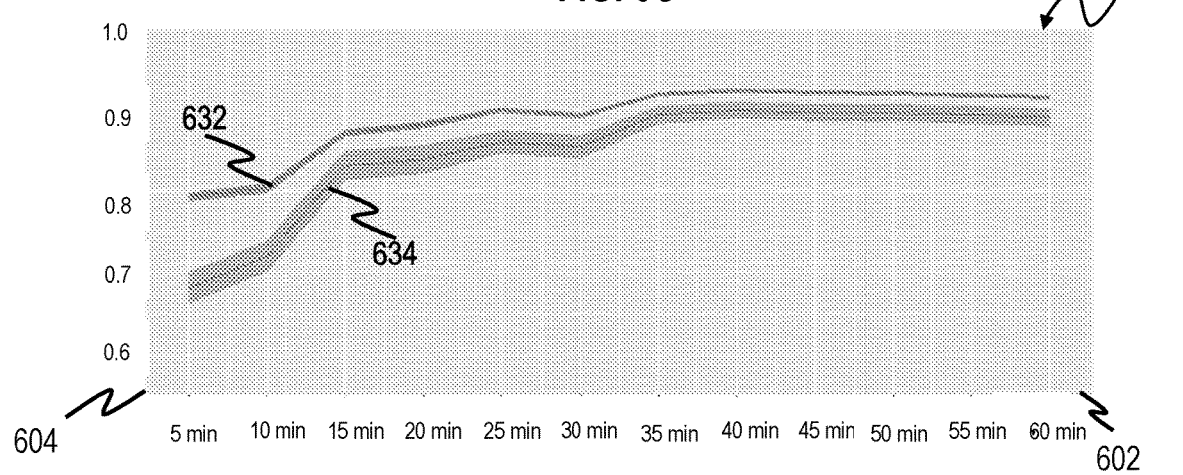

METHOD AND APPARATUS FOR PREDICTING A USE FOR A BLOOD TRANSFUSION

CROSS-REFERENCE TO RELATED APPLICATIONS

This application is a 371 national stage application of PCT Application No. PCT/US2017/032169 filed May 11, 2017 which claims benefit of Provisional Application No. 62/334,750 filed May 11, 2016 under 35 U.S.C. § 119(e), which is related to U.S. application Ser. No. 14/911,421 filed Feb. 10, 2016 a US 371 national stage application of international application PCT/US2014/050790 filed Aug. 12, 2014 which claims benefit of Provisional Application No. 61/864,832, filed Aug. 12, 2013, under 35 U.S.C. § 119(e).

STATEMENT OF GOVERNMENTAL INTEREST

This invention was made with government support under Grant Nos. FA8650-11-2-6D01, FA8650-13-2-6D11, and FA8650-15-2-6D26 awarded by the United States Air Force. The government has certain rights in the invention.

BACKGROUND OF THE INVENTION

When a patient suffers a trauma-related injury, they may experience massive blood loss. After admission to a medical facility, the patient may require a blood transfusion. However, a conventional method for determination of whether the patient requires the blood transfusion may not be made until after a substantial amount of time and a substantial amount of blood loss after sustaining an injury. Thus, it would be desirable to have a method for determining whether the patient requires the blood transfusion at an early stage of the treatment process. Various conventional methods have been proposed, for determining whether the patient requires the blood transfusion during the treatment process.

SUMMARY OF THE INVENTION

The conventional methods for determining whether a patient requires a blood transfusion are deficient in the timing and accuracy of the decision for use of the transfusion and in needing results from equipment not available in the pre-hospital arena or not immediately available when a trauma patient arrives even at a sophisticated trauma center. Therefore, a method and apparatus are provided for enhanced early prediction of the use for a blood transfusion.

In a first set of embodiments, a method is provided for predicting that a caregiver will order a blood transfusion during a treatment. The method includes obtaining, on a processor, first data that indicates values for one or more parameters of a characteristic of a peak of a Fourier transform of a continuous photoplethysmographic (PPG) waveform or of a continuous electrocardiogram (ECG) collected during the treatment or both. The method further includes applying, on the processor, coefficients to the values for the one or more parameters. The method further includes determining, on the processor, second data that indicates a prediction that the caregiver will order the blood transfusion during the treatment based on applying the coefficients to the values for the one or more parameters; and presenting on a display device output data based on the second data.

In some embodiments of the first set, the method further includes determining, on the processor, whether to order one or more blood units based on the prediction. In some embodiments of the first set, the first data is collected over a fixed time interval, the characteristic of the peak of the Fourier transform is one or more of a frequency, an amplitude and a power, and the parameters are one or more of a mean, a variance, a ratio of mean to median, a percentile and a Shannon entropy over the fixed time interval.

In a second set of embodiments, a method is provided for determining a model for predicting whether a caregiver will order a blood transfusion. The method includes obtaining, on a processor, data that indicates values for one or more parameters of a characteristic of a peak of a Fourier transform of a PPG waveform or of a ECG waveform or both during treatment of a plurality of patients. The method also includes assigning, on the processor, a result for each patient based on whether the patient received a blood transfusion during the treatment. The method also includes fitting, on the processor, the data to the results for the plurality of patients. The method also includes determining, on the processor, coefficients for the one or more parameters, to determine the model for predicting whether a caregiver will order a blood transfusion based on an input of the one or more parameters. The method also includes presenting, on a display device, output data based on the model.

In a third set of embodiments, an apparatus is provided for predicting that a caregiver will order a blood transfusion during a treatment. The apparatus includes a pulse oximeter configured to measure a PPG waveform and electrodes configured to measure a ECG waveform collected during a treatment of the patient. The apparatus further includes a display device and a processor connected to the pulse oximeter and the electrodes and configured to receive the PPG waveform, the ECG waveform or both. The apparatus further includes a memory including a sequence of instructions. The memory and the sequence of instructions are configured to, with the processor, cause the apparatus to perform a Fourier transform of the PPG waveform or the ECG waveform or both and to obtain first data that indicates values for one or more parameters of a characteristic of a peak of the Fourier transform of the PPG waveform or the ECG waveform or both. The memory and the sequence of instructions are configured to, with the processor, cause the apparatus to apply coefficients to the values for the one or more parameters, and determine second data that indicates a prediction that the caregiver will order the blood transfusion during the treatment based on applying the coefficients to the values for the one or more parameters. The memory and the sequence of instructions are configured to, with the processor, cause the apparatus to present on the display device output data based on the second data.

In a fourth set of embodiments, a computer-readable medium is provided carrying one or more sequences of instructions, where execution of the one or more sequences of instructions by a processor causes the processor to perform the steps of applying coefficients to values for one or more parameters of a characteristic of a peak of a Fourier transform of a PPG waveform or a ECG waveform or both collected during a treatment of a patient and determining a prediction that the caregiver will order a blood transfusion during the treatment based on applying the coefficients to the values for the one or more parameters. Execution of the one or more sequences of instructions by the processor causes the processor to present on a display device output data based on the prediction.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A is a block diagram that illustrates an example of an apparatus for predicting that a caregiver will order a blood transfusion during a treatment, according to one embodiment;

FIG. 3B is a flow diagram that illustrates an example of a method for determining a model for predicting whether a caregiver will order a blood transfusion, according to one embodiment;

FIG. 3C is a graph that illustrates an example of a receiver operating characteristic (ROC) curve, according to one embodiment;

FIG. 4 is a graph that illustrates an example of a PPG waveform, according to one embodiment;

FIG. 6A is a graph that illustrates an example of a plot of AUROC for a model using PPG waveform data versus data collection time of the PPG waveform data, according to one embodiment;

FIG. 6B is a graph that illustrates an example of a plot of AUROC for a model using ECG waveform data versus data collection time of the ECG waveform data, according to one embodiment;

FIG. 6C is a graph that illustrates an example of a plot of AUROC for a model using PPG and ECG waveform data versus data collection time of the PPG and ECG waveform data, according to one embodiment;

DETAILED DESCRIPTION

Figure 1B:
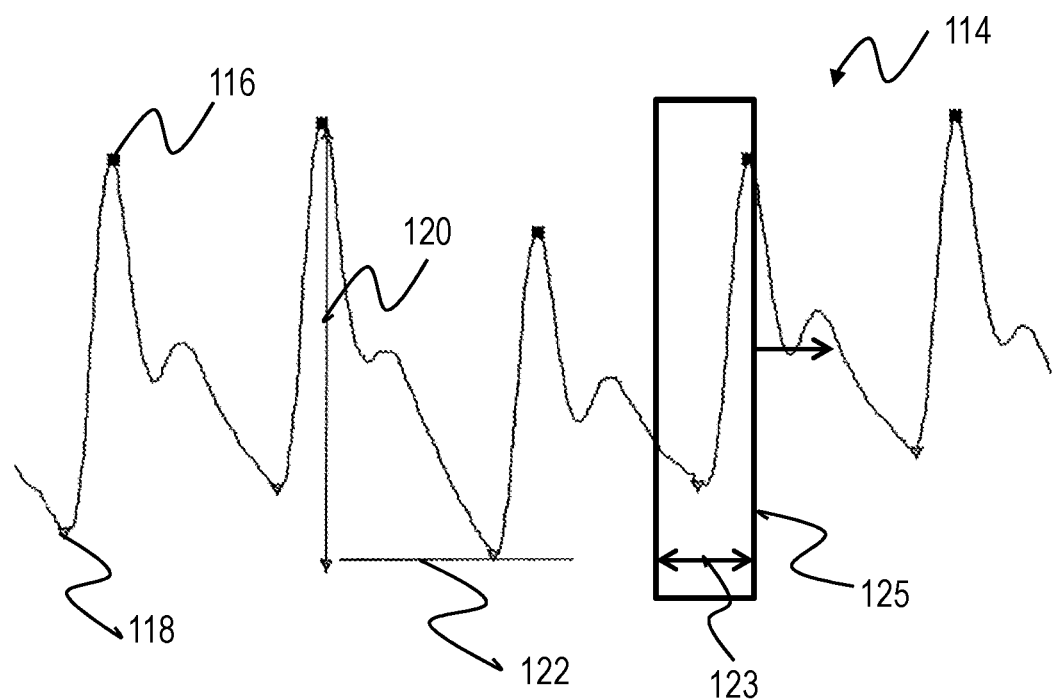
FIG. 1B is a graph that illustrates an example of a PPG waveform amplitude and period, according to one embodiment.

A method and apparatus are described for predicting that a caregiver will order a blood transfusion during a treatment. For purposes of the following description, a blood transfusion is defined as an instance in which a patient requires at least one unit of packed red blood cells (pRBC). One unit of pRBC has a volume of approximately 450 ml. pRBC are packed red blood cells that have been collected, centrifuged to pack them, processed, and stored in bags as blood units available for blood transfusion purposes. The red blood cells are mixed with an anticoagulant and storage solution which provides nutrients and aims to preserve the viability and functionality of the cells, which are stored at refrigerated temperatures. Additionally, a method and apparatus are described for predicting that a caregiver will order a massive blood transfusion. For purposes of the following description, a massive blood transfusion is defined as an instance in which a patient requires at least three units of pRBC. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of the treatment of patients at a medical facility including an emergency treatment vehicle. However, the invention is not limited to this context. In other embodiments, such as post-injury health care monitoring, detecting unexpected internal bleeding, and ruling out patients with internal bleeding in the field, the invention may be utilized.

1. Overview

When a patient suffers trauma, the first responders attend to the patient and begin treatment, often in the field or in an emergency response vehicle. This treatment often includes attaching vital signs monitors, such as a blood pressure sensor to measure blood pressure, a PPG sensor to measure oxygen saturation of the blood and electrodes to measure electrical activity of the heart. In some circumstances, the data from one or more of these sensors are used to determine blood loss, even due to hidden internal bleeding, and thus the probability of the use for a transfusion, including use for a massive transfusion. According to various embodiments, frequency characteristics of the data from one or more of these sensors are used to determine blood loss, and thus the probability of the use for a transfusion, including the use for a massive transfusion. In particular embodiments, characteristics of a peak of the Fourier transform of the PPG signal and/or ECG signal are exploited to make an enhanced prediction of the use for blood transfusion.

A blood-oxygen monitor, such as a pulse oximeter, measures the percentage of oxygen saturation of a patient's hemoglobin. More specifically, the pulse oximeter measures what percentage of hemoglobin (the protein in blood that carries oxygen) is loaded with oxygen. Acceptable ranges for patients without pulmonary pathology are from 95 to 99 percent. Pulse oximetry is a particularly convenient noninvasive measurement method. Typically, the pulse oximeter includes a processor and a pair of small light-emitting diodes (LEDs) facing a photodiode through a translucent part of the patient's body, usually a fingertip or an earlobe. One LED emits red light, with wavelength of about 660 nm, and the other LED emits infrared radiation, with a wavelength of about 940 nm. Absorption of light at these wavelengths differs significantly between arterial blood loaded with oxygen and venous blood with reduced oxygen. The changing absorption at each wavelength is measured during a pressure pulse of a cardiac cycle, allowing determination of the absorbances due to the pulsing arterial blood alone, excluding venous blood, skin, bone, muscle, fat and nail polish. The ratio of the red light measurement to the infrared light measurement is then calculated (which represents the ratio of oxygenated hemoglobin to deoxygenated hemoglobin), and this ratio is then converted to a percentage of $SpO_2$ by the processor via a lookup table. The pulse oximeter also uses the absorption data at each wavelength to determine a variation in blood volume in the skin caused by the pressure pulse during each cardiac cycle. The pulse oximeter generates the PPG waveform based on the variation in the blood volume over time and determines the pulse or heart rate (HR) of the patient based on the time gap between the peaks in the amplitude of the PPG waveform.

Electrocardiography (ECG or EKG) is the process of recording the electrical activity of the heart over a period of time using one or more electrodes placed on a patient's body. These electrodes detect the tiny electrical changes on the skin that arise from the heart muscle depolarizing during each heartbeat. In an example embodiment, a 12 lead ECG is used that includes ten electrodes which are placed on the patient's limbs and on the surface of the chest. The overall magnitude of the heart's electrical potential is then measured from twelve different angles ("leads") and is recorded over a period of time. In this way, the overall magnitude and direction of the heart's electrical depolarization is captured at each moment throughout the cardiac cycle. A waveform of voltage versus time produced by this noninvasive medical procedure is referred to as an electrocardiogram (abbreviated ECG or EKG). During each heartbeat, a healthy heart will have an orderly progression of depolarization that starts with pacemaker cells in the sinoatrial node, spreads out through the atrium, passes through the atrioventricular node down into the bundle of His and into the Purkinje fibers spreading down and to the left throughout the ventricles. This orderly pattern of depolarization gives rise to the characteristic ECG tracing. To the trained clinician, an ECG conveys a large amount of information about the structure of the heart and the function of its electrical conduction system. Among other things, an ECG can be used to measure the rate and rhythm of heartbeats, the size and position of the heart chambers, the presence of any damage to the heart's muscle cells or conduction system, the effects of cardiac drugs, and the function of implanted pacemakers. In an example embodiment, ten electrodes are used for a 12-lead ECG. The electrodes usually consist of a metal conductor covered with a conducting gel, embedded in the middle of a self-adhesive pad. The most common type of conductor for electrodes for ECG application is silver/silver chloride.

FIG. 1A is a block diagram that illustrates an example of a system 100 for predicting whether a caregiver will order a blood transfusion during a treatment, according to one embodiment. As illustrated in FIG. 1A, a system 100 includes a pulse oximeter 102 configured to measure a continuous photoplethysmographic (PPG) waveform collected during a treatment of a patient. As illustrated in FIG. 1A, a system 100 also includes one or more electrodes 106 configured to measure a continuous (ECG) waveform collected during a treatment of a patient. Although the system 100 of FIG. 1A depicts the pulse oximeter 102 and the electrodes 106, the system 100 need not include both of the pulse oximeter 102 and the electrodes 106 and may include either the pulse oximeter 102 or the electrodes 106, based on the availability of each sensor during treatment of the patient. Although the pulse oximeter 102 is depicted in FIG. 1A, any device may be used that is capable of measuring the continuous PPG waveform, as appreciated by one skilled in the art. Although the electrodes 106 are depicted in FIG. 1A, any device may be used that is capable of measuring the continuous ECG waveform, as appreciated by one skilled in the art.

As further illustrated in FIG. 1A, the system 100 includes a data processing system 104 connected to the pulse oximeter 102 and electrodes 106, to receive first data or to receive the sensor output from the electrodes 106 or pulse oximeter 102 or their equivalents and derive the first data. In some embodiments, if first data or sensor output from one of the pulse oximeter 102 or electrodes 106 is no longer available (e.g. one of the pulse oximeter 102 or electrodes 106 becomes detached during transport or patient motion), the data processing system 104 is configured to receive first data or sensor output from the other of the pulse oximeter 102 or electrodes 106. This embodiment advantageously ensures that the system 100 continues to predict whether to order the blood transfusion, in spite of data not being available from one of the electrodes 106 or pulse oximeter 102.

In one example embodiment, the first data is values for one or more parameters of a characteristic of the PPG waveform and/or the ECG waveform. In another example embodiment, the first data is values for one or more parameters of a characteristic of a Fourier transform of the PPG waveform and/or the ECG waveform, such as a characteristic of a peak of the Fourier transform. In another example embodiment, the first data is a threshold value of each of the parameters of the characteristic of the Fourier transform of the PPG waveform and/or the ECG waveform, such as the characteristic of the peak of the Fourier transform. The data processing system 104 includes a process 112 to predict whether the caregiver will order blood transfusion during the treatment. In some embodiments, the data processing system 104 is a computer system as described below with reference to FIG. 9 or a chip set described below with reference to FIG. 10. The process 112 is configured to receive or derive the first data and cause the system 100 to apply coefficients to the values of the one or more parameters of the first data and to determine second data that indicates a prediction that the caregiver will order the blood transfusion during the treatment based on applying the coefficients to the values of the one or more parameters. In one embodiment, the process 112 causes the system 100 to order one or more blood units, based on the prediction. However, the process 112 and the sequence of instructions need not be configured to cause the system 100 to order one or more blood units. The hardware used to form the data processing system 104 of the system 100 is described in more detail below in the Hardware Overview section. In one embodiment, the process 112 causes the system 100 to present output data on a display device based on the second data. In an example embodiment, the process 112 causes the system 100 to present the prediction on the display device.

In addition to the first data values of the one or more parameters of the characteristic of the PPG waveform, the data processing system 104 may receive third data that indicates values for one or more secondary parameters of a characteristic of the patient, such as an age and a gender of the patient, for example. FIG. 1A illustrates that the system 100 may include a manual input 108 such as a keyboard or a touchscreen, for example, to manually enter the age and/or gender of the patient whose first data is sent to the data processing system 104 from the pulse oximeter 102 and/or electrodes 106. Alternatively, FIG. 1A illustrates the system 100 may include a patient database 110 connected to the data processing system 104 such that the data processing system 104 may automatically retrieve the age and/or gender of the patient whose first data is sent to the data processing system 104 from the pulse oximeter 102 and/or electrodes 106. In one embodiment, the sequence of instructions of the process 112 may be configured to, with the data processing system 104, further cause the system 100 to apply coefficients to the values of the one or more secondary parameters of the patient and to further determine the second data that indicates the prediction that the caregiver will order the blood transfusion during the treatment based on applying the coefficients to the values of the one or more secondary parameters. However, the process 112 may be configured to, with the data processing system 104, cause the system 100 to determine the prediction based on merely applying the coefficients to the values of the first data and thus in these embodiments the system 100 need not include the manual input 108 and patient database 110.

Figure 2A:
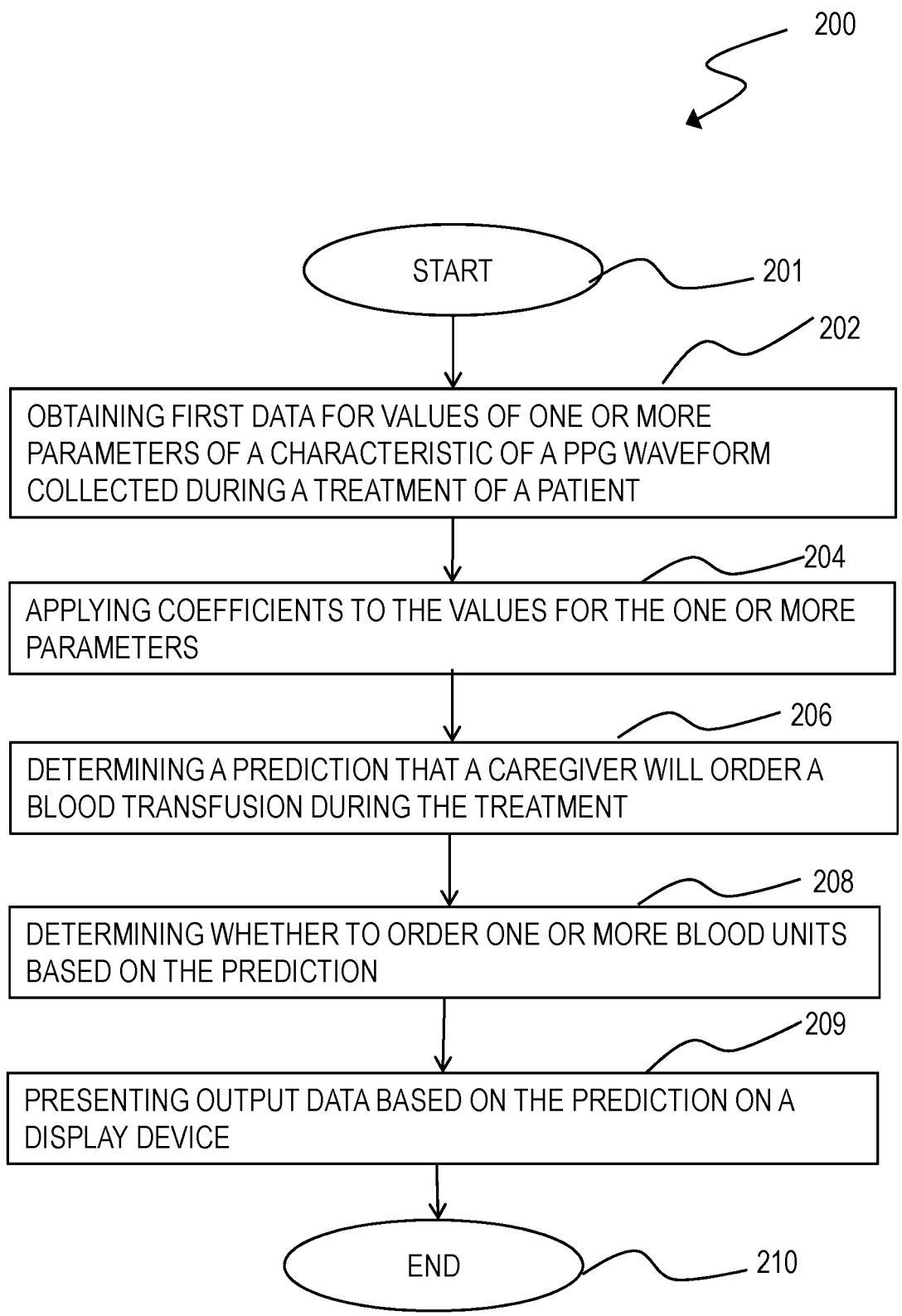
FIG. 2A is a flow diagram that illustrates an example of a method for predicting that a caregiver will order a blood transfusion during a treatment, according to one embodiment.
Figure 2B:
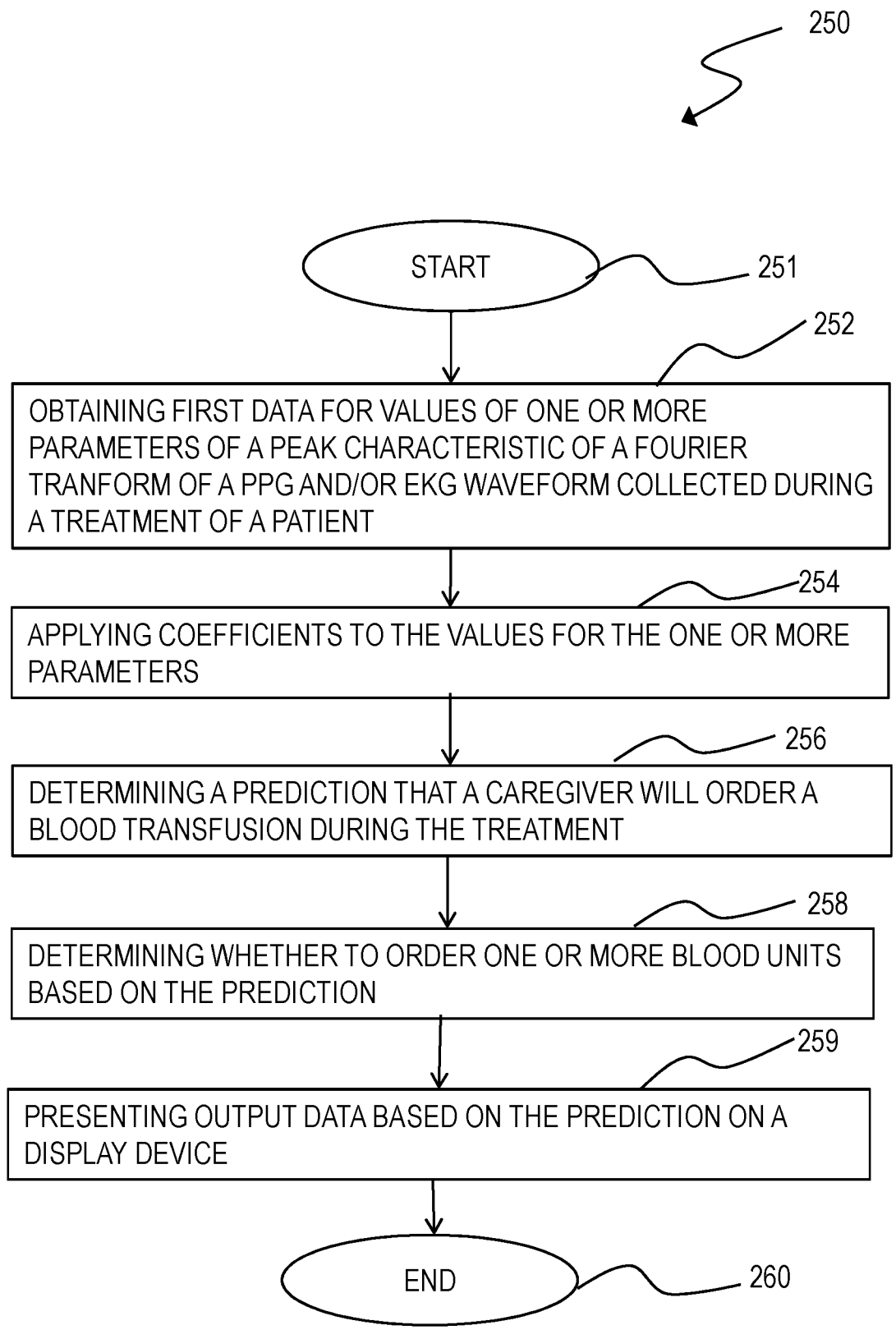
FIG. 2B is a flow diagram that illustrates an example of a method for predicting that a caregiver will order a blood transfusion during a treatment, according to one embodiment.
Figure 3A:
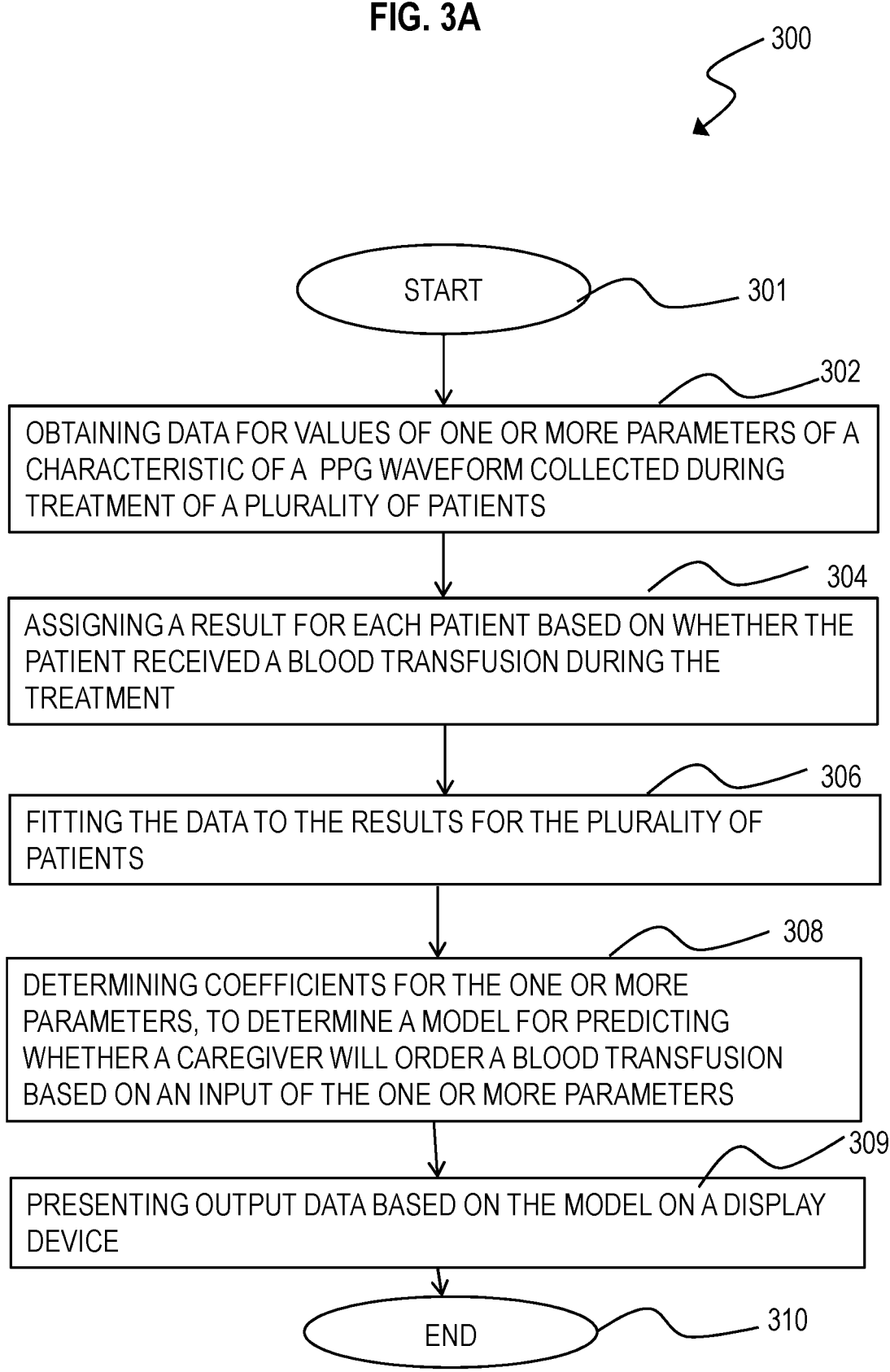
FIG. 3A is a flow diagram that illustrates an example of a method for determining a model for predicting whether a caregiver will order a blood transfusion, according to one embodiment.

As previously discussed, in one embodiment, the data processing system 104 receives first data that includes values for one or more parameters of a characteristic of the PPG waveform and/or the ECG waveform. FIG. 2A is a flow diagram that illustrates an example of a method 200 for predicting that a caregiver will order a blood transfusion during a treatment, according to one embodiment. Although the flow diagram of FIG. 2A, and subsequent flow diagrams in FIG. 2B, FIG. 3A and FIG. 3B, is each depicted as integral steps in a particular order for purposes of illustration, in other embodiments one or more steps, or portions thereof, are performed in a different order, or overlapping in time, in series or in parallel, or are deleted, or one or more other steps are added, or the method is changed in some combination of ways.

After starting at block 201, in step 202, first data is obtained, on the data processing system 104, that indicates values for one or more parameters of a characteristic of a PPG waveform collected during the treatment of the patient. In some embodiments, the first data is obtained by deriving the characteristics of the PPG waveform from the sensor data itself. In step 204, coefficients are applied, on the data processing system 104, to the values for the one or more parameters. In step 206, a prediction is determined, on the data processing system 104, that the caregiver will order a blood transfusion during the treatment. In step 208, a determination is made, on the data processing system 104, on whether to order one or more blood units, based on the prediction. In step 209, output data based on the prediction is presented on the display device, before the method ends at block 210. In an example embodiment, the output data is a determination of whether to order one or more blood units.

In one embodiment, the first data values of the one or more parameters are collected over a fixed time interval and the characteristic of the PPG waveform is one or more of a heart rate (HR) and an oxygen saturation ($SpO_2$). FIG. 1B is a graph that illustrates an example of a PPG waveform 114 including a peak 116, a valley 118 and an amplitude 120 that is measured between consecutive peaks and valleys 116, 118. Additionally, FIG. 1B illustrates that the heart rate 122 is measured based on the time between the peaks 116. As further illustrated in FIG. 1B, the amplitude 120 and heart rate 122 of the PPG waveform 114 varies with time. Thus, over the fixed time interval, a histogram of the amplitude 120 can be made to describe the variability of the amplitude 120 during the fixed time interval. Additionally, over the fixed time interval, a histogram of the heart rate 122 can be made to describe the variability of the heart rate 122 during the fixed time interval.

In another embodiment, the parameters include one or more of a percentage of the fixed time interval that the heart rate is below a threshold heart rate ("% time for HR<threshold"), a percentage of the fixed time interval that the oxygen saturation is below a threshold saturation ("% time for $SpO_2$<threshold"), a first percentile of the oxygen saturation over the fixed time interval ("first percentile $SpO_2$") and a second percentile of the oxygen saturation over the fixed time interval that is greater than the first percentile ("second percentile $SpO_2$"). In another embodiment, the parameter includes a percentile of an amplitude of the PPG waveform collected over the fixed time interval ("percentile PPG").

Figure 1C:
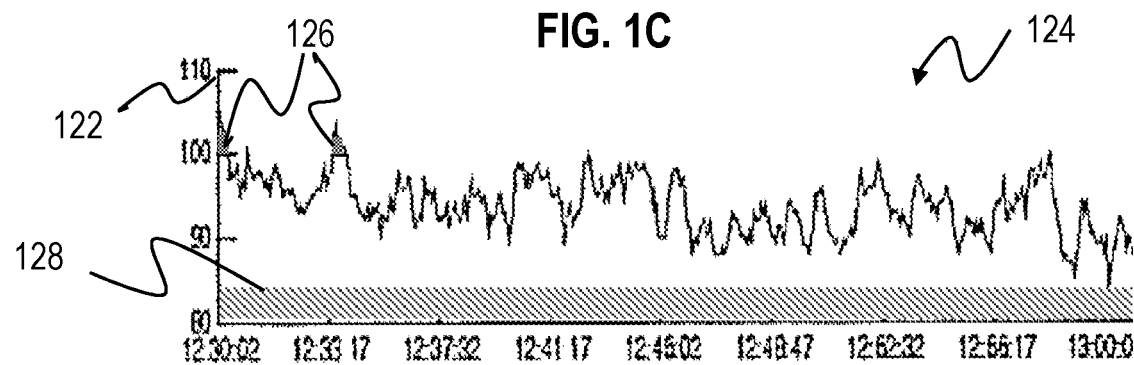
FIG. 1C is a graph that illustrates an example of a PPG heart rate waveform, according to one embodiment.
Figure 1D:
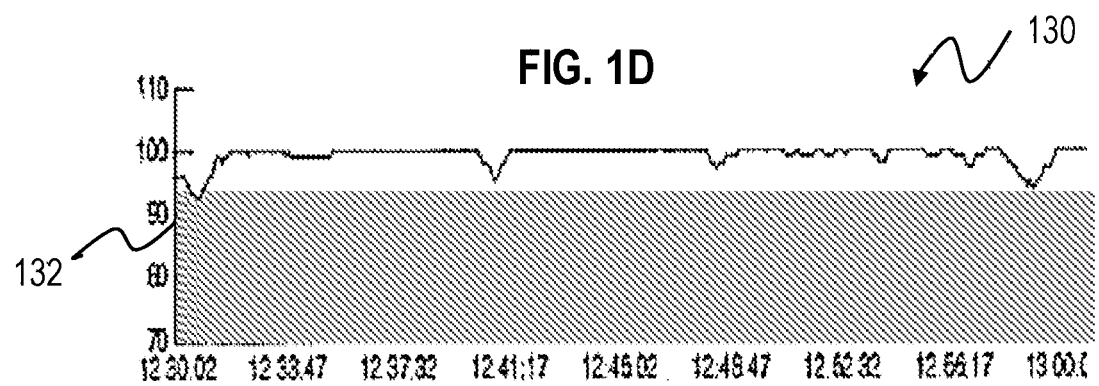
FIG. 1D is a graph that illustrates an example of a PPG oxygen saturation waveform, according to one embodiment.

In one embodiment, as illustrated in FIG. 1B, the pulse oximeter 102 generates the PPG waveform 114a heart rate waveform 124 illustrated in FIG. 1C and in an oxygen saturation waveform 130 illustrated in FIG. 1D. The heart rate waveform 124 depicts the heart rate 122 (distance between the peaks 116 of the PPG waveform 114) versus time, and the oxygen saturation waveform 130 depicts the percentage of $SpO_2$ in the blood versus time. In the embodiment, the parameter includes one or more of an area 128 of the heart rate waveform 124 below a low threshold heart rate or an area 126 above a high threshold heart rate and an area 132 of the oxygen saturation waveform 130 below a threshold oxygen saturation. In the example embodiment of FIG. 1B, the area 128 is based on a low threshold heart rate of about 72 beats per minute, the area 126 is based on a high threshold heart rate of about 100 beats per minute and the area 132 is based on a threshold oxygen saturation of about 92%. However, the areas 126, 128, 132 may be based on any threshold heart rate and threshold oxygen saturation. In other embodiments, the low threshold heart rate is selected in a range from about 60 beats per minute to about 100 beats per minute, the high threshold heart rate is selected in a range from about 100 beats per minute to about 150 beats per minute and the threshold oxygen saturation is selected in a range from about 85% to about 99%. In some embodiments, the above ranges are advantageously defined using one or more conditions (e.g. Bradycardia defined as <60 beats per minute, Tachycardia defined as >100 beats per minute and Supra-ventricular Tachycardia defined as >150 beats per minute).

In one embodiment, the prediction is based on a time range after the collection of the first data during which the patient will require the blood transfusion. The one or more parameters of the characteristic of the PPG waveform and the coefficients for the one or more parameters that are used to determine the prediction are based on the time range.

FIG. 3A a block diagram that illustrates an example of a method 300 for determining a model for predicting whether a caregiver will order a blood transfusion using first data that includes values for one or more parameters of a characteristic of the PPG waveform, according to one embodiment.

After starting at block 301, in step 302, data is obtained, on the data processing system 104, that indicates values for one or more parameters of a characteristic of a continuous PPG waveform during treatment of a plurality of patients. In step 304, a result is assigned, on the data processing system 104, for each patient based on whether the patient received a blood transfusion during the treatment. In step 306, the data is fitted, on the data processing system 104, to the results for the plurality of patients. In step 308, the coefficients are determined, on the data processing system 104, for the one or more parameters, to determine a model for predicting whether a caregiver will order a blood transfusion based on an input of the one or more parameters. In step 309, output data based on the model is presented on the display device, before the method ends at block 310.

In one embodiment, in step 304, the result is assigned for each patient during a plurality of time ranges of the treatment based on whether each patient received a blood transfusion during each of the time ranges. For example, the result is 1 if a patient receives a transfusion and zero if not. In some embodiments, the result is the number of units of blood the patient received. In the embodiment, in step 306, the data is fitted to each respective result for the plurality of patients during the plurality of time ranges. In the embodiment, in step 308, the coefficients are determined for the one or more parameters for each of the plurality of time ranges, to determine a model for predicting whether a caregiver will order a blood transfusion during each of the plurality of time ranges based on an input of one or more parameters.

In other embodiments, values of the coefficients are revised based on clinical data for the one or more parameters of the characteristic of the peak of the Fourier transform of at least one of the PPG waveform or ECG waveform during treatment of a plurality of patients. In an example embodiment, the clinical data is used in step 302 and the coefficients are revised in step 308 to improve the prediction based on the coefficients. In some embodiments, the values of the coefficients are continuously revised.

As previously discussed, in one embodiment, the data processing system 104 receives first data that includes values for one or more parameters of a peak characteristic of a Fourier transform of the PPG waveform and/or the ECG waveform. FIG. 2B is a flow diagram that illustrates an example of a method 250 for predicting that a caregiver will order a blood transfusion during a treatment, according to one embodiment.

After starting at block 251, in step 252, first data is obtained, on the data processing system 104, that indicates values for one or more parameters of a peak characteristic of a Fourier transform of the PPG waveform and/or the ECG waveform collected during the treatment of the patient. In some embodiments, the first data is obtained by determining the Fourier transform of the sensor signals using, for example, a digital Fast Fourier Transform (FFT), and deriving the characteristics of the transformed signal. In step 254, coefficients are applied, on the data processing system 104, to the values for the one or more parameters. In step 256, a prediction is determined, on the data processing system 104, that the caregiver will order a blood transfusion during the treatment. In step 258, a determination is made, on the data processing system 104, on whether to order one or more blood units, based on the prediction. In step 259, output data based on the prediction is presented on the display device, before the method ends at block 259. In an example embodiment, the output data is the determination of whether to order one or more blood units.

Figure 1E:
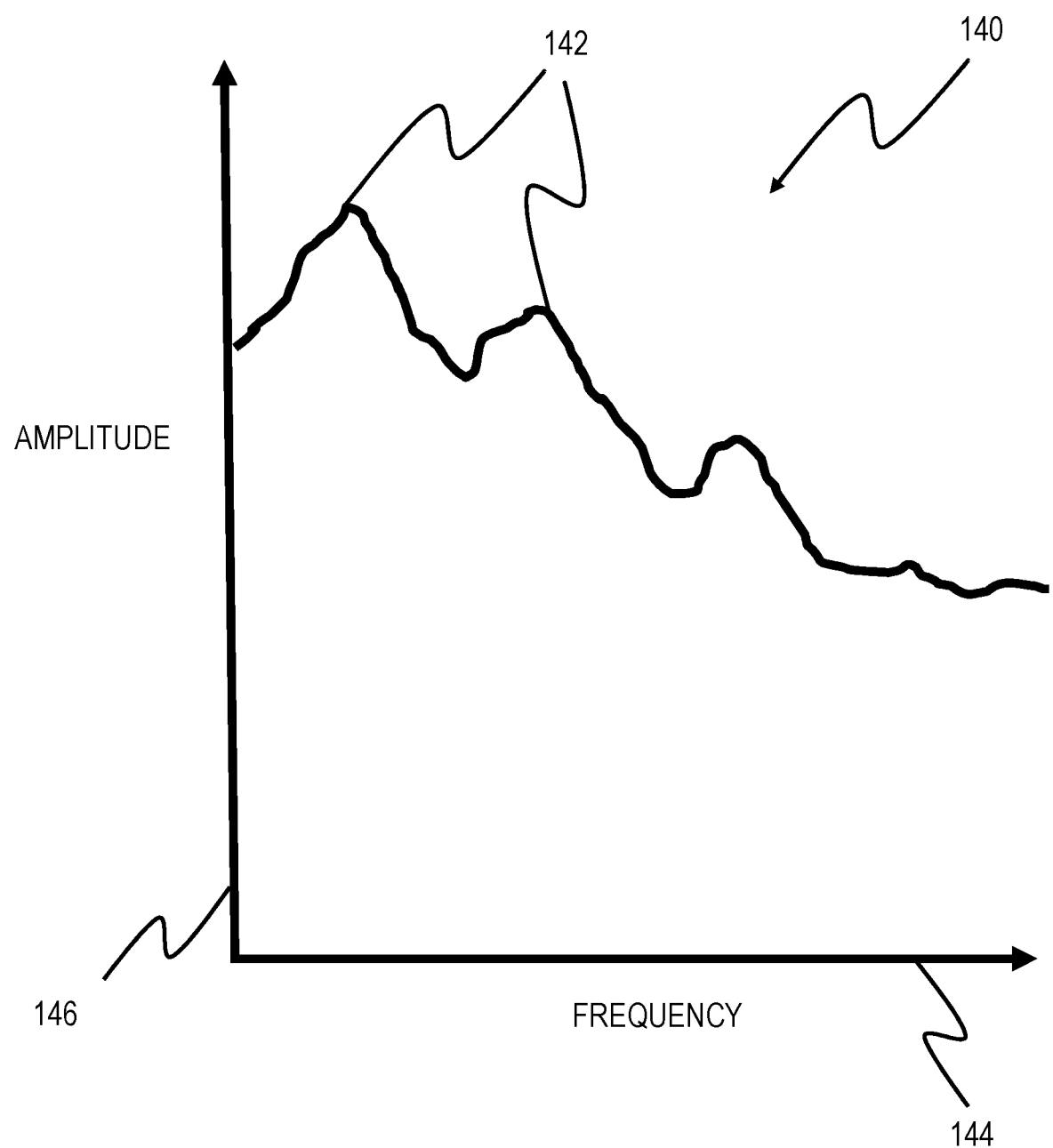
FIG. 1E is a graph that illustrates an example of a Fourier transform of the PPG waveform of FIG. 1B, according to one embodiment.

FIG. 1B illustrates a time window 125 with a width 123 that is less than the fixed time interval of the PPG waveform 114. In an example embodiment, the time window 125 is determined such that the PPG waveform 114 is stationary over the width 123 such that its frequency content does not change over the width 123. In an example embodiment, the width 123 is about 17 seconds. In other embodiments, the width 123 is selected in a range from about 5 seconds to about 600 seconds. In still other embodiments, where a patient is monitored in an unstable environment, the width 123 is selected in a range from about 15 seconds to about 60 seconds. FIG. 1E is a graph that illustrates an example of a Fourier transform 140 of the PPG waveform 114 of FIG. 1B over the time window 125, according to one embodiment. In an example embodiment, the Fourier transform 140 is a short time Fourier transform (STFT). The horizontal axis 144 is frequency and the vertical axis 146 is the amplitude of each respective frequency to the PPG waveform 114 in the time window 125. The Fourier transform 140 includes one or more local maxima or peaks 142. In one embodiment, the first data values of the one or more parameters are collected over a fixed time interval and the characteristic of the one or more peaks 142 of the Fourier transform 140 of the PPG waveform 114 is one or more of a frequency, an amplitude and a power. In one embodiment, as the time window 125 is moved over the fixed time interval of the PPG waveform 114, a respective Fourier transform 140 is performed over each time window 125. In an example embodiment, the time window 125 is moved by about one-fifth of a length of the time window 125. Thus, respective peak 142 characteristics are determined over the plurality of time windows 125 that encompass the fixed time interval of the PPG waveform 114. In an embodiment, the parameters of the peak 142 characteristic over the fixed time interval is one or more of a mean, a variance, a ratio of mean over median, a percentile, and a Shannon entropy. In an example embodiment, the parameters of the peak 142 characteristic include $10^{th}$ to $100^{th}$ percentiles and Shannon entropy for each peak 142 frequency, amplitude and power.

Figure 1F:
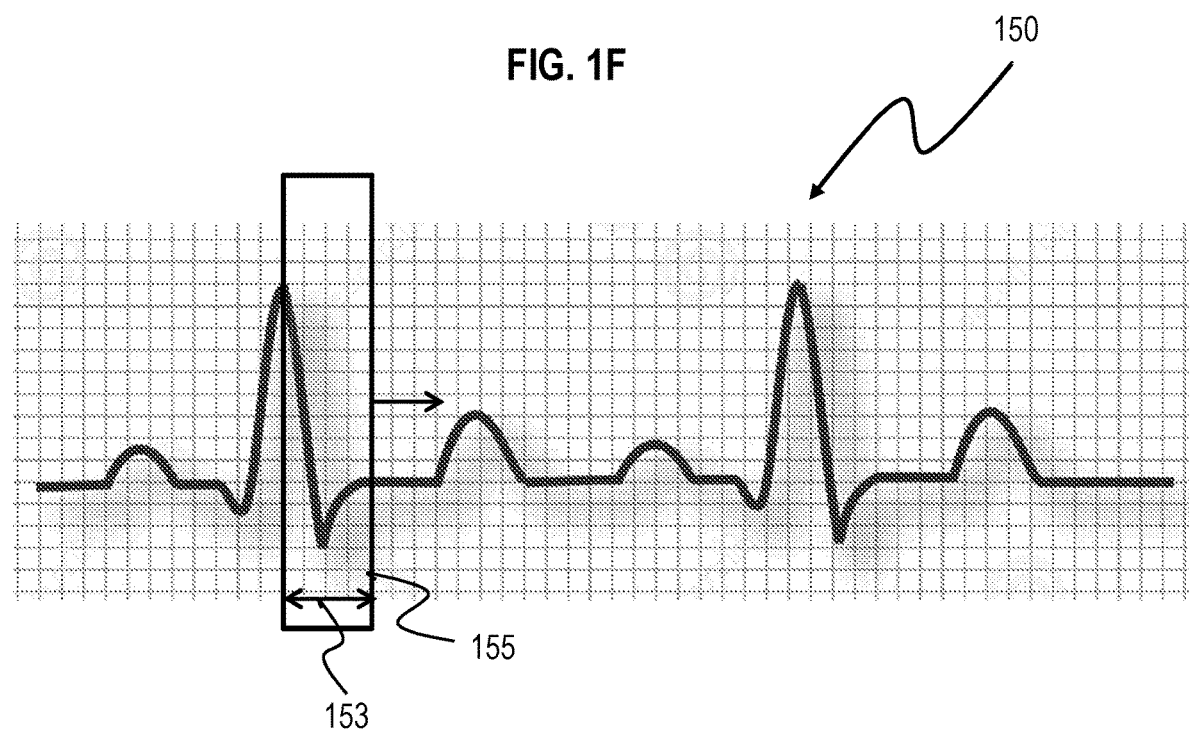
FIG. 1F is a graph that illustrates an example of an ECG waveform, according to one embodiment.
Figure 1G:
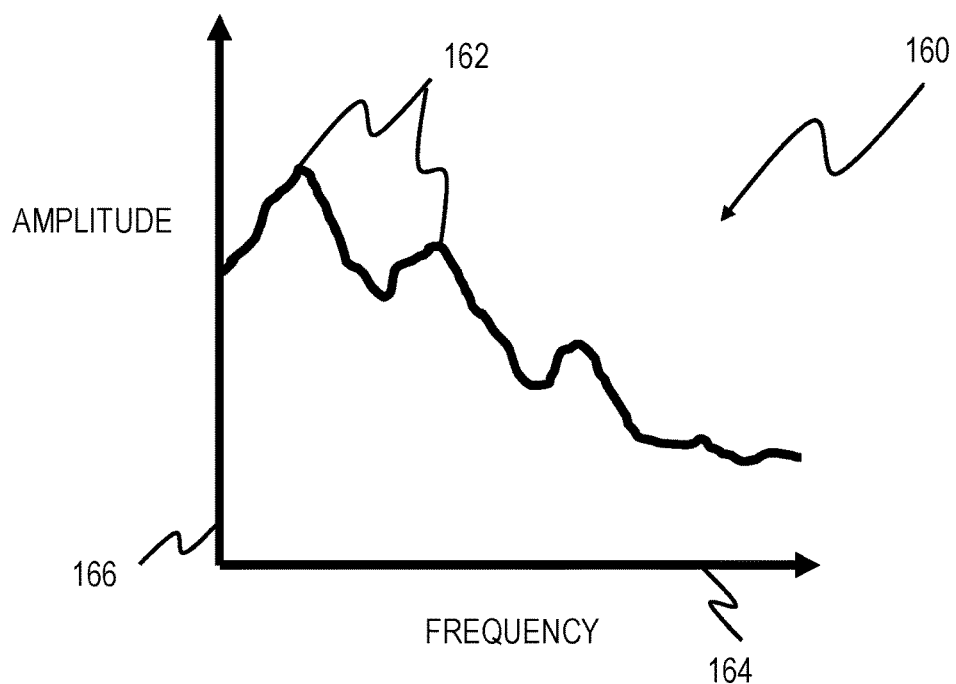
FIG. 1G is a graph that illustrates an example of a Fourier transform of the ECG waveform of FIG. 1F, according to one embodiment.

FIG. 1F is a graph that illustrates an example of an ECG waveform 150, according to one embodiment. As with the PPG waveform 114, the ECG waveform 150 includes a time window 155 with a width 153 that is less than the fixed time interval of the ECG waveform 150. In an example embodiment, the time window 155 is determined such that the ECG waveform 150 is stationary over the width 153 such that its frequency content does not change over the width 153. FIG. 1G is a graph that illustrates an example of a Fourier transform 160 of the ECG waveform 150 of FIG. 1F over the time window 155, according to one embodiment. In an example embodiment, the Fourier transform 160 is a short time Fourier transform (STFT). The horizontal axis 164 is frequency and the vertical axis 166 is the amplitude of each respective frequency to the ECG waveform 150 over the time window 155. The Fourier transform 160 includes one or more local maxima or peaks 162. In one embodiment, the first data values of the one or more parameters are collected over a fixed time interval and the characteristic of the one or more peaks 162 of the Fourier transform 160 of the ECG waveform 150 is one or more of a frequency, an amplitude and a power. In one embodiment, as the time window 155 is moved over the fixed time interval of the ECG waveform 150, a respective Fourier transform 160 is performed over each time window 155. Thus, respective peak 162 characteristics are determined over the plurality of time windows 155 encompassing the fixed time interval of the ECG waveform 150. In an embodiment, the parameters of the peak 162 characteristic over the fixed time interval is one or more of a mean, a variance, a ratio of mean over median, a percentile, and a Shannon entropy.

In an example embodiment, the method 250 of FIG. 2B is performed using first data that indicates values for one or more parameters of the peak 142 characteristic of the Fourier transform 140 of the PPG waveform 114. In this example embodiment, the data processing system 104 receives PPG waveform data from the pulse oximeter 102 but does not receive ECG waveform data from the electrodes 106. In this example embodiment, the electrodes 106 may not be connected to the data processing system 104 and/or are not available during treatment of the patient.

In an example embodiment, the method 250 of FIG. 2B is performed using first data that indicates values for one or more parameters of the peak 162 characteristic of the Fourier transform 160 of the ECG waveform 150. In this example embodiment, the data processing system 104 receives ECG waveform data from the electrodes 106 but does not receive PPG waveform data from the pulse oximeter 102. In this example embodiment, the pulse oximeter 102 may not be connected to the data processing system 104 and/or are not available during treatment of the patient.

In an example embodiment, the method 250 of FIG. 2B is performed using first data that indicates values for one or more parameters of the peak 142 characteristic of the Fourier transform 140 of the PPG waveform 114 and values for one or more parameters of the peak 162 characteristic of the Fourier transform 160 of the ECG waveform 150.

In one embodiment, the prediction is based on a time range after the collection of the first data during which the patient will require the blood transfusion. The one or more parameters of the peak 142 characteristic of the Fourier transform 140 of the PPG waveform 114 and/or the peak 162 characteristic of the Fourier transform 160 of the ECG waveform 150 and the coefficients for the one or more parameters that are used to determine the prediction are based on the time range.

FIG. 3B a block diagram that illustrates an example of a method 350 for determining a model for predicting whether a caregiver will order a blood transfusion using first data that includes values for one or more parameters of a peak 142 characteristic of the Fourier transform 140 of the PPG waveform 114 and/or a peak 162 characteristic of the Fourier transform 160 of the ECG waveform 150, according to one embodiment. After starting at block 351, in step 352, data is obtained on the data processing system 104 that indicates values for one or more parameters of the peak 142 characteristic of the Fourier transform 140 of the continuous PPG waveform 114 and/or the peak 162 characteristic of the Fourier transform 160 of the continuous ECG waveform 150 during treatment of a plurality of patients. In step 354, a result is assigned on the data processing system 104 for each patient based on whether the patient received a blood transfusion during the treatment. In step 356, the data is fitted on the data processing system 104 to the results for the plurality of patients. In step 358, the coefficients are determined, on the data processing system 104 for the one or more parameters to determine a model for predicting whether a caregiver will order a blood transfusion based on an input of the one or more parameters. In step 359, output data based on the model is presented on the display device, before the method ends at block 359.

In one embodiment, in step 354, the result is assigned for each patient during a plurality of time ranges of the treatment based on whether each patient received a blood transfusion during each of the time ranges. For example, the result is 1 if a patient receives a transfusion and zero if not. In some embodiments, the result is the number of units of blood the patient received. In the embodiment, in step 356, the data is fitted to each respective result for the plurality of patients during the plurality of time ranges. In the embodiment, in step 358, the coefficients are determined for the one or more parameters for each of the plurality of time ranges, to determine a model for predicting whether a caregiver will order a blood transfusion during each of the plurality of time ranges based on an input of one or more parameters.

2. Example Embodiments

FIG. 4 is a graph that illustrates an example of a PPG waveform 414, according to one embodiment. The horizontal axis 402 is time measured in seconds, and the vertical axis 404 is amplitude of the PPG waveform 414 measured in millivolts (mV). As with the PPG waveform 114, the PPG waveform 414 has a time window 425 with a width 423 that is less than the fixed time interval of the PPG waveform 114. The Fourier transform 140 is determined over the time window 425, before the time window 425 is moved by a time increment τ and the Fourier transform 140 is determined over the next time window 425. As depicted in FIG. 4, the time increment τ is less than the width 423 such that the Fourier transforms 140 are determined over time windows 425 that are overlapping and noncontiguous. In another embodiment, the time increment τ is approximately equal to the width 423 such that the transforms 140 are determined over time windows 425 that are non-overlapping and contiguous. In another embodiment, the time increment τ is greater than the width 423 such that the transforms 140 are determined over time windows 425 that are non-overlapping and non-contiguous. In an example embodiment, the width 423 is less than 30 seconds. In an example embodiment, the width 423 is approximately 17 seconds.

Figure 5A:
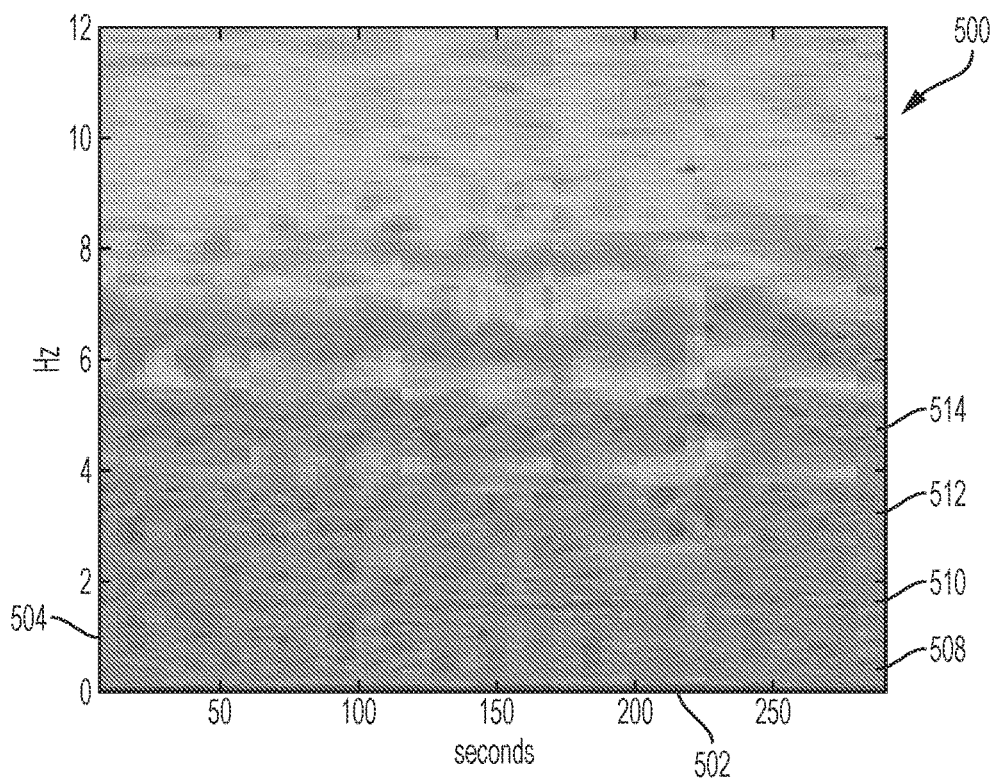
FIG. 5A is a surface that illustrates an example of a spectrogram of the PPG waveform of FIG. 4, according to one embodiment.
Figure 5B:
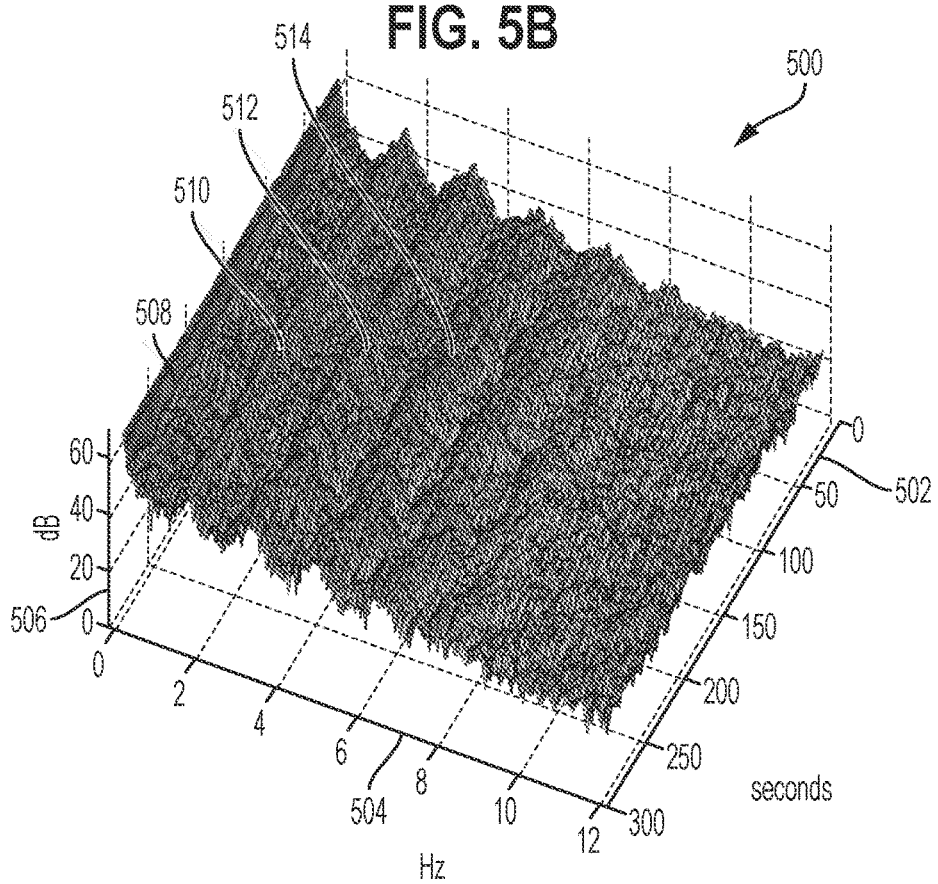
FIG. 5B is a 3D graph that illustrates a 3D perspective view of the spectrogram of FIG. 5A, according to one embodiment.

FIG. 5A is a surface that illustrates an example of a spectrogram 500 of the PPG waveform 414 of FIG. 4, according to one embodiment. FIG. 5B is a 3D graph that illustrates a 3D perspective view of the spectrogram 500 of FIG. 5A, according to one embodiment. The first axis 502 is time measured in units of seconds, the second axis 504 is frequency measured in units of Hertz (Hz) and the third axis 506 is amplitude measured in units of decibels (dB), which is represented by greyscale in FIG. 5A. The spectrogram 500 is formed by combining the Fourier transforms 140 determined over the time windows 425 encompassing the fixed time interval of the PPG waveform 414. In an example embodiment, the Fourier transforms 140 for each time window 425 are stacked along the first axis 502 to form the spectrogram 500. As shown in FIGS. 5A-5B, the spectrogram 500 includes four local maxima or peaks 508, 510, 512, 514 that represent four local maxima or peaks of the Fourier transforms 140 taken over the time windows 425 encompassing the fixed time interval of the PPG waveform 414. In an example embodiment, a frequency of the peak 508 varies within a range from about 0 to about 1 Hz over the fixed time interval of the PPG waveform 414; a frequency of the peak 510 varies within a range from about 1 to about 3 Hz over the fixed time interval of the PPG waveform 414; a frequency of the peak 512 varies within a range from about 3 to about 4 Hz over the fixed time interval of the PPG waveform 414 and a frequency of the peak 512 varies within a range from about 5 to about 6 Hz over the fixed time interval of the PPG waveform 414. In one embodiment, the frequency of the peak 508 is attributed to either the heart rate (HR) or respiration rate. In an example embodiment, the frequency of the peak 508 is attributed to the HR when the frequency is about 1.0 Hz. In another example embodiment, the frequency of the peak 508 is attributed to the respiration rate when the frequency is about 0.3 Hz.

In an example embodiment of the method 250 of FIG. 2B, in step 252 values of one or more parameters of a characteristic of one or more of the peaks 508, 510, 512, 514 are collected. In step 252, a Fourier transform 140 is determined for each of the plurality of time windows 425 encompassing the fixed time interval of the PPG waveform 414. In step 252, the Fourier transforms 140 for each time window 425 are then axially stacked in the direction of the first axis 502 to form the spectrogram 500. In step 252, the peaks 508, 510, 512, 514 are then identified in the spectrogram 500. In an example embodiment, the characteristic of one or more of the peaks 508, 510, 512, 514 is one or more of a frequency, an amplitude and a power. In an example embodiment, the parameters of the characteristic is one or more of a mean, a variance, a ratio of mean over median, a percentile, and a Shannon entropy. However, the method 250 is not limited to using characteristics of the four peaks 508, 510, 512, 514 and may use characteristics of less or more than these four peaks in the spectrogram 500. Additionally, the method 250 is not limited to using characteristics of peaks of the spectrogram 500 and may use other characteristics of the spectrogram 500.

Figure 5C:
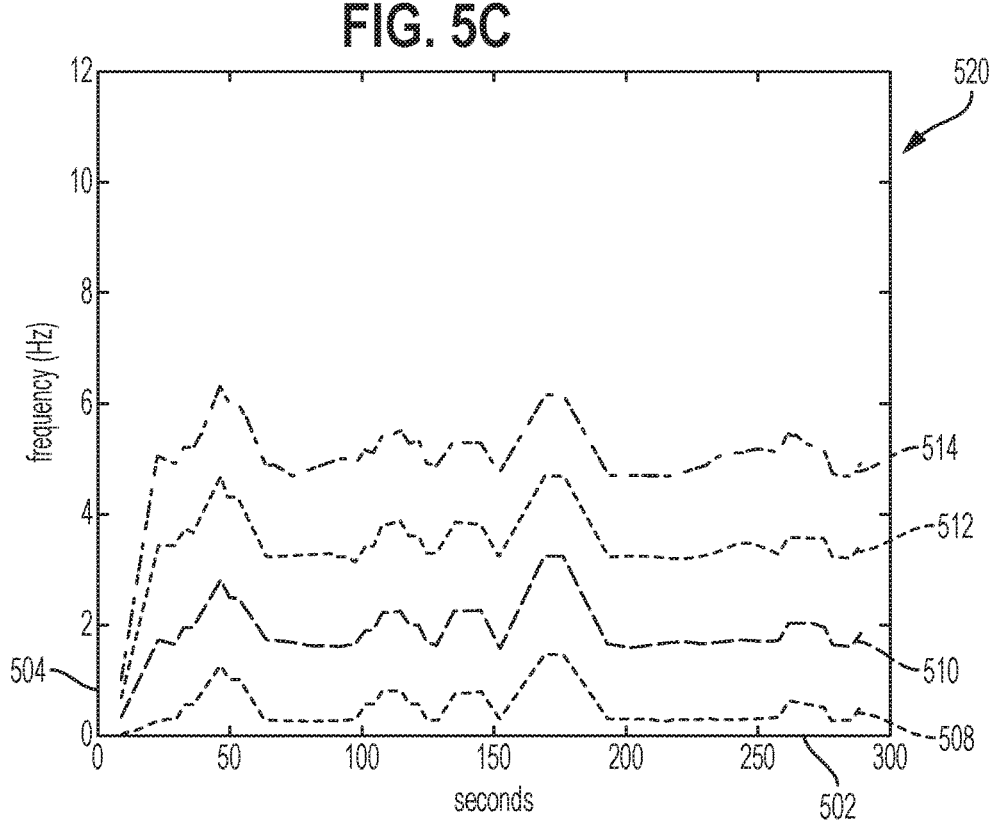
FIG. 5C is a graph that illustrates an example of a plot of frequency versus time for one or more peaks of the spectrogram of FIG. 5A, according to one embodiment.
Figure 5D:
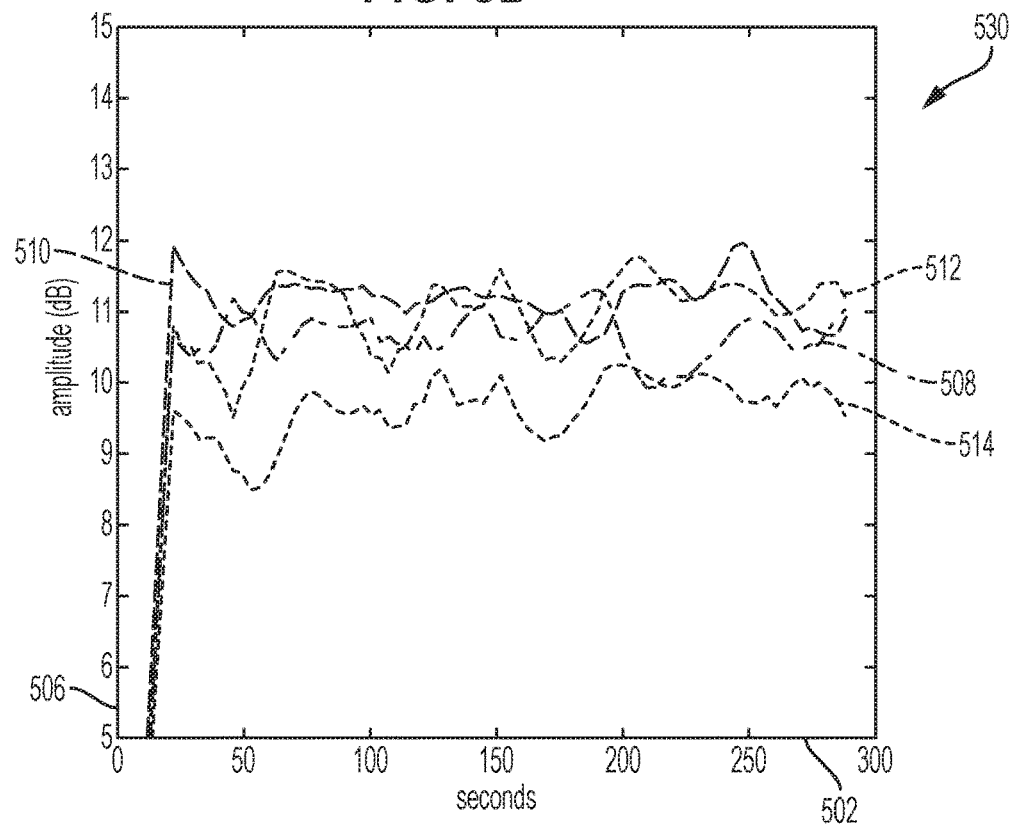
FIG. 5D is a graph that illustrates an example of a plot of amplitude versus time for one or more peaks of the spectrogram of FIG. 5A, according to one embodiment.

FIG. 5C is a graph that illustrates an example of a plot 520 of frequency versus time for one or more peaks 508, 510, 512, 514 of the spectrogram 500 of FIG. 5A, according to one embodiment. The horizontal axis 502 is time in units of seconds (sec) and the vertical axis 504 is frequency in units of Hertz (Hz). The plot 520 depicts the variation of the frequency of each peak 508, 510, 512, 514 over the fixed time interval of the PPG waveform 414. FIG. 5D is a graph that illustrates an example of a plot 530 of amplitude versus time for one or more peaks 508, 510, 512, 514 of the spectrogram 500 of FIG. 5A, according to one embodiment. The horizontal axis 502 is time in units of seconds (sec) and the vertical axis 506 is amplitude in units of decibels (dB). The plot 530 depicts the variation of the amplitude of each peak 508, 510, 512, 514 over the fixed time interval of the PPG waveform 414.

In an example embodiment, a spectrogram of the ECG waveform 150 is determined, in a similar manner as the spectrogram 500 of the PPG waveform 414 discussed above. In an example embodiment of the method 250 of FIG. 2B, in step 252, a Fourier transform 160 is determined for each of a plurality of time windows 155 encompassing the fixed time interval of the ECG waveform 150. In step 252, the Fourier transforms 160 are then axially stacked to form the spectrogram of the ECG waveform 150. In step 252, the peaks of the spectrogram of the ECG waveform 150 are then identified. In an example embodiment, the characteristic of one or more of the spectrogram peaks is one or more of a frequency, an amplitude and a power. In an example embodiment, the parameters of the characteristic is one or more of a mean, a variance, a ratio of mean over median, a percentile, and a Shannon entropy. In an example embodiment, variations of the spectrogram 500 are observed in a range from about 0 Hz to about 20 Hz.

In an example embodiment of the method 250 of FIG. 2B, in step 252, values of one or more parameters of a characteristic of one or more of the peaks of the spectrogram 500 of the PPG waveform 414 and one or more of the peaks of a spectrogram of the ECG waveform 150 are collected.

According to an example embodiment, the first data values of the one or more parameters are collected over one or more fixed time intervals, such as 15 minutes, 30 minutes and/or 60 minutes, for example. In other embodiments, a first fixed time interval is selected in a range from about 0 minutes to about 15 minutes, a second fixed time interval is selected in a range from about 15 minutes to about 30 minutes and a third fixed time interval is selected in a range from about 30 minutes to about 60 minutes. In some embodiments, selecting a value of the fixed time interval near a lower end of the above ranges advantageously provides a more immediate prediction whether the caregiver will order the blood transfusion. In other embodiments, selecting a value of the fixed time interval near an upper end of the above ranges advantageously provides a more accurate prediction whether the caregiver will order the blood transfusion.

According to another example embodiment, the parameters of the methods 250, 350 of FIGS. 2B, 3B include one or more of a 10 percentile, a 20 percentile, a 30 percentile, a 40 percentile, a 50 percentile, a 60 percentile, a 70 percentile, a 80 percentile, a 90 percentile and a 100 percentile of the peak 142 characteristic of the Fourier transform 140 of the PPG waveform 114 and/or the peak 162 characteristic of the Fourier transform 160 of the ECG waveform 150.

According to another example embodiment, the parameters of the methods 200, 300 of FIGS. 2A, 3A include one or more of a percentage of the fixed time interval that the heart rate is below a threshold heart rate of about 60 beats per minute, a percentage of the fixed time interval that the oxygen saturation is below a threshold saturation of about 95%, a first percentile of about 25 percentile of the oxygen saturation over the fixed time interval and/or a second percentile of about 50 percentile of the oxygen saturation over the fixed time interval. In other embodiments, the threshold heart rate is selected in a range from about 50 beats per minute to about 75 beats per minute, the threshold saturation is selected in a range from about 85% to about 99%, the first percentile is selected in a range from about 10 percentile to about 60 percentile and the second percentile is selected in a range from about 30 percentile to about 80 percentile.

In an example embodiment, a plurality of predictions are determined, based on whether the caregiver will order a blood transfusion during each of a plurality of time ranges after the collection of the first data, such as within 3 hours, within 6 hours, within 12 hours and within 24 hours after the collection of the first data. In other embodiments, a first time range is selected in a range from about 1 hour to 5 hours, a second time range is selected in a range from about 4 hours to about 8 hours, a third time range is selected in a range from about 8 hours to about 16 hours and a fourth time range is selected in a range from about 16 hours to about 32 hours. In some embodiments, selecting a value of the time range near a lower end of the above ranges advantageously provides a more immediate prediction whether the caregiver will order the blood transfusion. In other embodiments, selecting a value of the time range near an upper end of the above ranges advantageously provides a more accurate prediction whether the caregiver will order the blood transfusion.

TABLE 1

Range of coefficient values and recommended coefficient values for each parameter including Patient Demographics, based on data collection over a fixed time interval of about 15 minutes

| | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 1 | Age | −0.018-0.014 | −0.002 | −0.022-0.01 | −0.004 | −0.02-0.012 | −0.002 | −0.01-0.02 | 0.005 |
| 2 | Sex | 0.436-1.964 | 1.151 | 0.55-2.25 | 1.337 | 0.18-1.45 | 0.784 | 0.31-1.59 | 0.918 |
| 3 | PreH-HR | −0.044-0.008 | −0.026 | −0.0-−0.012 | −0.03 | −0.04-−0.008 | −0.023 | −0.044-−0.02 | −0.03 |
| 4 | 10 percentile PPG | −0.005-−0.001 | −0.003 | −0.01-−0.004 | −0.008 | −0.005-−0.002 | −0.003 | | |
| 5 | 20 percentile PPG | | | | | | | −0.03-−0.008 | −0.018 |
| 6 | 30 percentile PPG | | | | | | | 0.006-0.03 | 0.017 |
| 7 | 40 percentile PPG | | | 0.002-0.011 | 0.007 | | | | |
| 8 | 50 percentile PPG | | | | | | | | |
| 9 | 60 percentile PPG | | | | | | | | |
| 10 | 70 percentile PPG | | | | | | | | |
| 11 | 80 percentile PPG | | | | | | | | |
| 12 | 90 percentile PPG | | | −0.006-−0.0003 | −0.003 | | | −0.004-0.0002 | −0.002 |
| 13 | 25 percentile PPG | | | | | | | | |
| 14 | 75 percentile PPG | | | | | | | | |
| 15 | 25-75 percentile PPG | | | | | | | | |
| 16 | % time for SPO2 < 98% | | | | | | | | |
| 17 | Dose for SPO2 < 98% | | | | | | | | |
| 18 | % time for SPO2 < 95% | 0.052-3.450 | 1.806 | −0.63-3.10 | 1.30 | | | 0.41-3.82 | 2.154 |
| 19 | Dose for SPO2 < 95% | 0.059-0.367 | 0.211 | | | 0.041-0.265 | 0.147 | 0.07-0.40 | 0.233 |
| 20 | % time for SPO2 < 92% | | | | | | | | |
| 21 | Dose for SPO2 < 92% | | | | | | | | |
| 22 | % time for SPO2 < 90% | | | | | | | | |
| 23 | Dose for SPO2 < 90% | | | | | | | | |

TABLE 1-continued

Range of coefficient values and recommended coefficient values for each parameter including Patient Demographics, based on data collection over a fixed time interval of about 15 minutes

| | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 24 | % time for SPO2 < 86% | | | 2.45-9.45 | 5.801 | | | | |
| 25 | Dose for SPO2 < 86% | | | | | | | | |
| 26 | 25 percentile SPO2 | 0.329-2.677 | 1.492 | 0.41-2.94 | 1.65 | −0.11-1.72 | 0.814 | | |
| 27 | 50 percentile SPO2 | 0.038-2.114 | 1.085 | 0.005-2.19 | 1.105 | −0.05-1.81 | 0.89 | | |
| 28 | 75 percentile SPO2 | | | | | | | | |
| 29 | mean SP02 | | | | | | | | |
| 30 | % time for HR > 120 | | | | | | | | |
| 31 | Dose for HR > 120 | | | | | | | | |
| 32 | % time for HR > 110 | −0.094-0.01 | −0.04 | −0.11-0.001 | −0.05 | | | | |
| 33 | Dose for HR > 110 | | | | | | | | |
| 34 | % time for HR > 100 | | | | | | | | |
| 35 | Dose for HR > 100 | | | | | | | | 0.008-0.34 | 0.176 |
| 36 | % time for HR < 72 | | | | | | | | |
| 37 | Dose for HR < 72 | 0.045-0.421 | 0.232 | 0.036-0.417 | 0.225 | | | | |
| 38 | % time for HR < 60 | 0.844-4.973 | 2.86 | 0.849-5.182 | 2.96 | 0.41-2.80 | 1.608 | 1.11-3.31 | 2.224 |
| 39 | Dose for HR < 60 | | | | | | | | |
| 40 | 25 percentile HR | | | | | | | | |
| 41 | 50 percentile HR | | | | | | | | |
| 42 | 75 percentile HR | | | | | | | | |
| 43 | mean HR | | | | | | | | |
| 44 | Intercept | −43.4-4.95 | −24.14 | −41.91-−2.72 | −22.22 | −1.94-1.77 | −0.085 | −34.2-0.143 | −17.05 |
| 45 | Thresholds Range | 0.5-1.0 | 0.5 | 0.5-1.0 | 0.5 | 0.5-1.0 | 0.5 | 0.5-1.0 | 0.5 |

Table 1 provides a list of one or more parameters that are used to determine the prediction in the method 200 of FIG. 2A, and a 95% confidence interval range of the coefficients for the parameters for each time range, to determine the prediction for each time range. Additionally, Table 1 also provides a list of the recommended coefficient values within the coefficient interval ranges, for each parameter. Blank entries in Table 1 represent zero value coefficients, and thus parameters that are not deemed useful in the model. The coefficient ranges of the parameters listed in Table 1 are based on the first data collection over a fixed time interval of about 15 minutes. Table 2 is also provided, which lists the range of coefficient values and the recommended coefficient values for each parameter, based on the first data being collection over a fixed time interval of about 30 minutes. Similarly, Table 3 is also provided, which lists the range of coefficient values and the recommended coefficient values for each parameter, based on the first data being collection over a fixed time interval of about 60 minutes. The parameters listed in Tables 1-3 are discussed here. The age and gender parameters of the patient were previously discussed and may be manually or automatically input into the data processing system 104. In an example embodiment, the gender parameter may be input numerically as 0 for female and 1 for male. The pre-hospital heart rate ("PreH-HR") parameter is a measure of the patient's heart rate prior to the arrival at the hospital or medical facility and is performed prior to the measurement of the patient's heart rate with the pulse oximeter 102. In some embodiments, pre-hospital parameters (e.g. "PreH-HR") and coefficients for pre-hospital parameters can be used to determine the prediction using the method 200 of FIG. 2A.

TABLE 2

Range of coefficient values and recommended coefficient values for each parameter including Patient Demographics, based on data collection over a fixed time interval of about 30 minutes

| | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 1 | Age | −0.024-0.014 | −0.004 | −0.018-0.018 | −4.8E-06 | −0.017-0.014 | −0.0014 | −0.009-0.021 | 0.006 |

TABLE 2-continued

Range of coefficient values and recommended coefficient values for each parameter including Patient Demographics, based on data collection over a fixed time interval of about 30 minutes

|  | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 2 | Sex | 0.217-2.034 | 1.057 | 0.434-2.09 | 1.204 | 0.273-1.618 | 0.910 | 0.289-1.611 | 0.917 |
| 3 | PreH-HR | −0.04-−0.005 | −0.025 | −0.04-−0.006 | −0.023 | −0.043-−0.013 | −0.028 | −0.042-−0.011 | −0.027 |
| 4 | 10 percentile PPG | −0.006-−0.002 | −0.004 | −0.009-−0.0035 | −0.0065 | −0.005-−0.0013 | −0.003 | −0.0044-−0.001 | −0.0027 |
| 5 | 20 percentile PPG | | | | | | | | |
| 6 | 30 percentile PPG | | | | | | | | |
| 7 | 40 percentile PPG | | | | | | | | |
| 8 | 50 percentile PPG | | | | | | | | |
| 9 | 60 percentile PPG | | | | | | | | |
| 10 | 70 percentile PPG | | | | | | | | |
| 11 | 80 percentile PPG | | | | | | | | |
| 12 | 90 percentile PPG | | | −0.014-−0.002 | −0.008 | | | | |
| 13 | 25 percentile PPG | | | | | | | | |
| 14 | 75 percentile PPG | | | | | | | | |
| 15 | 25-75 percentile PPG | | | | | | | | |
| 16 | % time for SPO2 < 98% | | | | | | | | |
| 17 | Dose for SPO2 < 98% | | | | | | | | |
| 18 | % time for SPO2 < 95% | | | | | | | | −0.736-3.143 | 1.285 |
| 19 | Dose for SPO2 < 95% | | | | | | | | |
| 20 | % time for SPO2 < 92% | | | | | | | | |
| 21 | Dose for SPO2 < 92% | | | | | | | | |
| 22 | % time for SPO2 < 90% | | | | | | | | |
| 23 | Dose for SPO2 < 90% | | | −0.674-0.103 | −0.272 | | | | |
| 24 | % time for SPO2 < 86% | 3.819-14.01 | 8.79 | 6.016-23.175 | 14.34 | 4.57-13.09 | 8.71 | 3.846-12.615 | 8.04 |
| 25 | Dose for SPO2 < 86% | | | | | | | | |
| 26 | 25 percentile SPO2 | | | 0.684-4.17 | 2.382 | | | | |
| 27 | 50 percentile SPO2 | | | | | | | 0.650-3.317 | 1.965 |
| 28 | 75 percentile SPO2 | | | −0.395-7.158 | 3.435 | | | | |
| 29 | mean SP02 | −15.34-2.05 | −6.63 | | | −10.97-1.111 | −4.98 | | |
| 30 | % time for HR > 120 | | | | | | | | |
| 31 | Dose for HR > 120 | | | | | | | | |
| 32 | % time for HR > 110 | 0.007-1.029 | 0.516 | | | 0.034-0.70 | 0.371 | | |
| 33 | Dose for HR > 110 | | | | | | | | |
| 34 | % time for HR > 100 | | | | | | | | |
| 35 | Dose for HR > 100 | | | | | | | | |
| 36 | % time for HR < 72 | | | −1.694-−0.15 | −0.853 | | | | |
| 37 | Dose for HR < 72 | 0.186-0.698 | 0.427 | 0.147-0.591 | 0.362 | 0.136-0.538 | 0.330 | 0.112-0.551 | 0.333 |

TABLE 2-continued

Range of coefficient values and recommended coefficient values for each parameter including Patient Demographics, based on data collection over a fixed time interval of about 30 minutes

|   | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 38 | % time for HR < 60 | | | 0.241-3.788 | 2.03 | | | | |
| 39 | Dose for HR < 60 | −1.07-−0.025 | −0.547 | | | −0.727-−0.242 | −0.381 | −0.148-0.14 | −0.062 |
| 40 | 25 percentile HR | −0.08-0.002 | −0.04 | −0.088-0.006 | −0.041 | | | | |
| 41 | 50 percentile HR | | | | | | | | |
| 42 | 75 percentile HR | −0.008-0.057 | 0.025 | | | | | 0.029-0.0823 | 0.055 |
| 43 | mean HR | | | | | | | | |
| 44 | Intercept | −69.86-−17.38 | −42.08 | −56.65-−10.68 | −32.94 | −53.60-−12.97 | −32.61 | −61.13-−16.04 | −38.69 |
| 45 | Thresholds Range | 0.5-1.0 | 0.5 | 0.5-1.0 | 0.5 | 0.5-1.0 | 0.5 | 0.5-1.0 | 0.5 |

TABLE 3

Range of coefficient values and recommended coefficient values for each parameter including Patient Demographics, based on data collection over a fixed time interval of about 60 minutes

|   | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 1 | Age | −0.022-0.014 | −0.004 | −0.023-0.011 | −0.0057 | −0.019-0.011 | −0.004 | −0.011-0.018 | 0.0033 |
| 2 | Sex | 0.323-2.073 | 1.134 | 0.402-1.950 | 1.126 | 0.231-1.552 | 0.860 | 0.289-1.611 | 0.917 |
| 3 | PreH-HR | −0.044-−0.008 | −0.026 | −0.041-−0.008 | −0.0245 | −0.039-−0.009 | −0.024 | −0.042-−0.011 | −0.027 |
| 4 | 10 percentile PPG | −0.007-0.0026 | −0.0047 | −0.007-−0.003 | −0.0049 | −0.006-−0.0025 | −0.004 | −0.0044-−0.001 | −0.0027 |
| 5 | 20 percentile PPG | | | | | | | | |
| 6 | 30 percentile PPG | | | | | | | | |
| 7 | 40 percentile PPG | | | | | | | | |
| 8 | 50 percentile PPG | | | | | | | | |
| 9 | 60 percentile PPG | | | | | | | | |
| 10 | 70 percentile PPG | | | | | | | | |
| 11 | 80 percentile PPG | | | | | | | | |
| 12 | 90 percentile PPG | | | | | | | | |
| 13 | 25 percentile PPG | | | | | | | | |
| 14 | 75 percentile PPG | | | | | | | | |
| 15 | 25-75 percentile PPG | | | | | | | | |
| 16 | % time for SPO2 < 98% | | | | | | | | |
| 17 | Dose for SPO2 < 98% | | | | | | | | |
| 18 | % time for SPO2 < 95% | | | | | | | | −0.736-3.143 | 1.285 |
| 19 | Dose for SPO2 < 95% | | | | | | | | |
| 20 | % time for SPO2 < 92% | | | | | | | | |
| 21 | Dose for SPO2 < 92% | | | −1.07-−0.080 | −0.550 | | | | |
| 22 | % time for SPO2 < 90% | | | | | | | | |

TABLE 3-continued

Range of coefficient values and recommended coefficient values for each parameter including Patient Demographics, based on data collection over a fixed time interval of about 60 minutes

| | Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|---|
| 23 | Dose for SPO2 < 90% | | | | | −0.936-−0.259 | −0.461 | | |
| 24 | % time for SPO2 < 86% | 7.618-27.77 | 17.26 | 11.16-35.25 | 22.70 | 9.094-29.37 | 18.93 | 3.846-12.615 | 8.04 |
| 25 | Dose for SPO2 < 86% | | | | | | | | |
| 26 | 25 percentile SPO2 | | | | | | | | |
| 27 | 50 percentile SPO2 | | | | | | | 0.650-3.317 | 1.965 |
| 28 | 75 percentile SPO2 | | | | | | | | |
| 29 | mean SP02 | 1.274-3.80 | 2.55 | | | | | | |
| 30 | % time for HR > 120 | | | −0.278-0.042 | −0.120 | −0.265-0.034 | −0.116 | | |
| 31 | Dose for HR > 120 | −0.033-0.570 | 0.259 | | | | | | |
| 32 | % time for HR > 110 | | | 0.025-0.280 | 0.153 | 0.025-0.260 | 0.143 | | |
| 33 | Dose for HR > 110 | | | | | | | | |
| 34 | % time for HR > 100 | | | | | | | | |
| 35 | Dose for HR > 100 | | | 0.114-0.460 | 0.281 | 0.107-0.426 | 0.262 | | |
| 36 | % time for HR < 72 | | | | | | | | |
| 37 | Dose for HR < 72 | 0.088-0.655 | 0.373 | | | | | 0.112-0.551 | 0.333 |
| 38 | % time for HR < 60 | | | | | | | | |
| 39 | Dose for HR < 60 | | | | | | | −0.148-0.14 | −0.062 |
| 40 | 25 percentile HR | | | | | | | | |
| 41 | 50 percentile HR | | | | | | | | |
| 42 | 75 percentile HR | | | | | | | 0.029-0.0823 | 0.055 |
| 43 | mean HR | | | | | | | | |
| 44 | Intercept | −99.40-−29.89 | −62.66 | −45.23-−10.69 | −27.44 | −41.91-−9.83 | −25.40 | −61.13-−16.04 | −38.69 |
| 45 | Thresholds Range | 0.5-1.0 | 0.5 | 0.5-1.0 | 0.5 | 0.5-1.0 | 0.5 | 0.5-1.0 | 0.5 |

Additional parameters obtained in the method 200 of FIG. 2A include one or more percentiles of an amplitude of the PPG waveform ("percentile PPG") over the fixed time interval. The amplitude percentiles may be determined by the data processing system 104 based on the received first data or determined by the pulse oximeter 102 and subsequently transmitted to the data processing system 104. The percentiles of the amplitude of the PPG waveform may be one or more of 10 percentile, 20 percentile, 30 percentile, 40 percentile, 50 percentile, 60 percentile, 70 percentile, 80 percentile, 90 percentile, 25 percentile, 75 percentile and a difference between the 25 and 75 percentile.

Additional parameters obtained in the method 200 of FIG. 2A include a percentage of the fixed time interval that the oxygen saturation is below a threshold saturation, such as about 98%, 95%, 92%, 90% and 86% ("% time for SpO2"). In other embodiments, a first threshold saturation is selected in a range from about 95% to about 99%, a second threshold saturation is selected in a range from about 92% to about 98%, a third threshold saturation is selected in a range from about 90% to about 95%, a fourth threshold saturation is selected in a range from about 86% to about 92% and a fifth threshold saturation is selected in a range from about 82% to about 90%. In some embodiments, selection of the threshold saturation within the above ranges advantageously provides additional information regarding a status of the patient. In an example embodiment, a saturation in a range of 95-100% is considered normal, a saturation below 90% is associated with abnormal content, i.e. a rapid decrease in arterial oxygen content and a saturation below 86% is associated with even further abnormal content.

Additional parameters obtained in the method 200 of FIG. 2A include an area of the oxygen saturation waveform below the threshold saturations ("Dose for SpO2"). Additional parameters include a 25 percentile, a 50 percentile, a 75 percentile and a mean of the oxygen saturation level during the fixed time interval. For example, the 25 percentile of the oxygen saturation level may be that, during 25% of the fixed time interval, the oxygen saturation was at a level of 98% or higher.

Additional parameters obtained in the method 200 of FIG. 2A include a percentage of the fixed time interval that the heart rate is below a low threshold heart rate, such as about 60 beats per minute or 72 beats per minute, or above a high threshold heart rate, such as about 100 beats per minute, 110 beats per minute or 120 beats per minute ("% time for HR"). Additional parameters include an area of the heart rate waveform below the low threshold heart rate or above the high threshold heart rate ("Dose for HR"). Additional parameters include a 25 percentile, a 50 percentile, a 75 percentile and a mean of the heart rate level during the fixed time interval. For example, the 25 percentile of the heart rate level may be that, during 25% of the fixed time interval, the heart rate was at a level of 100 beats per minute or higher.

The coefficient ranges listed in Table 1 encompass all coefficient values and coefficient ranges that are within the listed ranges in Table 1. The parameters that may be used to determine the prediction are not limited to those parameters listed in Table 1 and include any parameter that is derived from a characteristic of the PPG waveform or an identifying characteristic of the patient. Additionally, the ranges of the coefficients for the parameters listed in Table 1 are not limited to the specific numerical ranges listed in Table 1.

Table 1 lists a range for an intercept that is used to form the equation for determining the prediction for each time range. The formula for the prediction (P) in steps 208, 258 of the methods 200, 250 for each time range is based on the following equation:

$$P = C_1 * V_1 + C_2 * V_2 + \ldots + I$$

Where $V_1$ is the first value of a first parameter, $V_2$ is the second value of a second parameter, and $C_1$ and $C_2$ are the respective first and second coefficients for the first and second parameters, based on Table 1. Additionally, I is the intercept for the specific time range within which the prediction P is being made, based on Table 1. Although the prediction (P) formula above merely lists two values for two parameters and two coefficients, less or more than two parameters and two coefficients may be used to determine the prediction.

As shown in Table 1, for the time range of up to 3 hours after the collection of the first data, the coefficient range for the percentage of the fixed time interval that the heart rate is below the threshold heart rate of about 60 beats per minute is in a range from about 0.84 to about 4.93. Additionally, the coefficient range for the percentage of the fixed time interval that the oxygen saturation is below the threshold saturation of about 95% is in a range from about 0.05 to about 3.45. Additionally, the coefficient range for the 25 percentile of the oxygen saturation is in a range from about 0.33 to about 2.68 and the coefficient for the 50 percentile of the oxygen saturation is in a range from about 0.04 to about 2.11. In an example embodiment, the above parameters with the largest magnitude coefficients may be used to determine the prediction for the time range of up to 3 hours after the collection of the first data. However, fewer or more than the above listed parameters may be used to determine the prediction.

As shown in Table 1, for the time range of up to 6 hours after the collection of the first data, the coefficient range for the percentage of the fixed time interval that the heart rate is below the threshold heart rate of about 60 beats per minute is in a range from about 0.85 to about 5.18. Additionally, the coefficient range for the percentage of the fixed time interval that the oxygen saturation is below the threshold saturation of about 86% is in a range from about 2.45 to about 9.45. Additionally, the coefficient range for the 25 percentile of the oxygen saturation is in a range from about 0.41 to about 2.93 and the coefficient for the 50 percentile of the oxygen saturation is in a range from about 0.01 to about 2.20. In an example embodiment, the above parameters with the largest magnitude coefficients may be used to determine the prediction of whether the caregiver will order the blood transfusion within 6 hours after the collection of the first data. However, fewer or more than the above listed parameters may be used to determine the prediction.

As shown in Table 1, for the time range of up to 12 hours after the collection of the first data, the coefficient range for the percentage of the fixed time interval that the heart rate is below the threshold heart rate of about 60 beats per minute is in a range from about 0.41 to about 2.80. Additionally, the coefficient range for the percentage of the fixed time interval that the oxygen saturation is below the threshold saturation of about 95% is in a range from about 0.04 to about 0.26. Additionally, the coefficient range for the 25 percentile of the oxygen saturation is in a range from about −0.11 to about 1.72 and the coefficient for the 50 percentile of the oxygen saturation is in a range from about −0.05 to about 1.81. In an example embodiment, the above parameters with the largest magnitude coefficients may be used to determine the prediction of whether the caregiver will order the blood transfusion within 12 hours after the collection of the first data. However, less or more than the above listed parameters may be used to determine the prediction.

As shown in Table 1, for the time range of up to 24 hours after the collection of the first data, the coefficient range for the percentage of the fixed time interval that the heart rate is below the threshold heart rate of about 60 beats per minute is in a range from about 1.11 to about 3.31. Additionally, the coefficient range for the percentage of the fixed time interval that the oxygen saturation is below the threshold saturation of about 95% is in a range from about 0.41 to about 3.82. In an example embodiment, the above parameters with the largest magnitude coefficients may be used to determine the prediction of whether the caregiver will order the blood transfusion within 24 hours after the collection of the first data. However, less or more than the above listed parameters may be used to determine the prediction.

Additionally, as shown in Table 1, for the prediction determination within each time range, a threshold range for the prediction is about 0.5-1.0. Thus, if the calculated prediction (P) is above 0.5, the patient is likely in need of a transfusion within the time range. If the calculated prediction is between 0.2 and 0.5, then further investigation, such as further collection of the first data, may be necessary. If the calculated prediction is below 0.2, then the patient is likely not in need of a transfusion within the time range after the collection of the first data. In an example embodiment, the data processing system 104 may include a display to output the prediction and/or may transmit a signal to a remote location such as a blood bank at a proximate location to the hospital, for example, to order one or more blood units, based on the prediction in excess of 0.5, for example.

Table 4 provides a list of one or more parameters that are used to determine the prediction in the method 250 of FIG. 2B, and a 95% confidence interval range of the coefficients for the parameters for each time range, to determine the prediction for each time range. Additionally, Table 4 also provides a list of the recommended coefficient values within the coefficient interval ranges, for each parameter. The coefficient ranges of the parameters listed in Table 4 are based on the first data collection over a fixed time interval of about 5 minutes. Table 5 is also provided, which lists the range of coefficient values and the recommended coefficient values for each parameter, based on the first data being collected over a fixed time interval of about 15 minutes. Similarly, Table 6 is also provided, which lists the range of coefficient values and the recommended coefficient values for each parameter, based on the first data being collected over a fixed time interval of about 30 minutes. Similarly, Table 7 is also provided, which lists the range of coefficient values and the recommended coefficient values for each parameter, based on the first data being collected over a fixed time interval of about 55 minutes. The parameters listed in Tables 4-7 are discussed here. In an example embodiment, the PPG Peak1 Max Power parameter is a maximum power of the peak 508 of the spectrogram 500 over a time period along the horizontal axis 502. In an example embodiment, the PPG Peak2 10$^{th}$ Percentile parameter is a 10$^{th}$ percentile of the peak 510 of the spectrogram 500 over a time period along the horizontal axis 502. In an example embodiment, the PPG Maximum Median Amplitude parameter is a maximum of the median amplitudes of the peaks 508, 510, 512, 514 over a time period along the horizontal axis 502. In an example embodiment, the ECG Peak3 Maximum Amplitude parameter is a maximum amplitude of a third peak (equivalent to peak 512 in spectrogram 500) of an ECG spectrogram over a time period. In an example embodiment, the ECG Peak2 Power σ parameter is a standard deviation of a power of a second peak (equivalent to peak 510 in spectrogram 500) of an ECG spectrogram over a time period. In an example embodiment, the Intercept parameter is the intercept (I) used in the prediction equation (P) above.

TABLE 4

Range of coefficient values and recommended coefficient values for each parameter, based on data collection over a fixed time interval of about 5 minutes

| Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|
| 1 PPG Peak1 Max power | 0.184-0.937 | 0.453 | 0.184-0.991 | 0.495 | 0.125-0.943 | 0.476 | 0.107-0.849 | 0.397 |
| 2 PPG Peak2 10$^{th}$ percent | −0.674-−0.200 | −0.462 | −0.614-−0.133 | −0.395 | −0.518-−0.045 | −0.295 | −0.524-−0.087 | −0.328 |
| 3 PPG Max Med Amp | 0.023-0.309 | 0.160 | 0.022-0.276 | 0.145 | 0.033-0.271 | 0.148 | 0.040-0.269 | 0.152 |
| 4 ECG Peak3 Max Amp | −0.157-0.197 | −0.013 | −0.106-0.261 | 0.040 | −0.055-0.357 | 0.103 | −0.048-0.354 | 0.107 |
| 5 ECG Peak2 Power σ | −0.122-0.699 | 0.295 | −0.208-0.566 | 0.191 | −0.335-0.431 | 0.070 | −0.293-0.443 | 0.092 |
| 6 Intercept | −41.926-2.223 | −4.588 | −50.043-−2.443 | −11.256 | −53.672-−0.348 | −17.132 | −45.355-1.571 | −10.226 |

TABLE 5

Range of coefficient values and recommended coefficient values for each parameter, based on data collection over a fixed time interval of about 15 minutes

| Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|
| 1 PPG Peak1 Maxpower | 0.249-1.402 | 0.819 | 0.406-1.454 | 0.930 | 0.280-1.263 | 0.767 | 0.262-1.197 | 0.716 |
| 2 PPG Peak2 10$^{th}$ percent | −0.580-−0.107 | −0.310 | −0.513-−0.073 | −0.265 | −0.549-−0.089 | −0.295 | −0.571-−0.109 | −0.320 |
| 3 PPG Max Med Amp | 0.007-0.427 | 0.211 | 0.006-0.368 | 0.183 | 0.029-0.360 | 0.191 | 0.040-0.357 | 0.195 |
| 4 ECG Peak3 Max Amp | 0.267-1.735 | 0.987 | 0.490-1.804 | 1.135 | 0.747-1.991 | 1.358 | 0.698-1.893 | 1.285 |
| 5 ECG Peak2 Power σ | 0.324-1.304 | 0.801 | 0.171-1.055 | 0.602 | 0.131-0.969 | 0.541 | 0.118-0.933 | 0.517 |
| 6 Intercept | −92.567-−10.554 | −50.577 | −98.850-−20.262 | −60.548 | −88.458-−15.327 | −50.843 | −82.329-−12.546 | −45.237 |

TABLE 6

Range of coefficient values and recommended coefficient values for each parameter, based on data collection over a fixed time interval of about 30 minutes

| Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|
| 1 PPG Peak1 Max power | 0.275-1.403 | 0.840 | 0.447-1.444 | 0.944 | 0.297-1.229 | 0.764 | 0.309-1.209 | 0.760 |
| 2 PPG Peak2 10$^{th}$ percent | −0.291-−0.069 | −0.173 | −0.258-−0.043 | −0.148 | −0.259-−0.042 | −0.146 | −0.266-−0.048 | −0.150 |

TABLE 6-continued

Range of coefficient values and recommended coefficient values for each parameter, based on data collection over a fixed time interval of about 30 minutes

| Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|
| 3 PPG Max Med Amp | 0.035-0.504 | 0.263 | 0.003-0.399 | 0.196 | 0.040-0.403 | 0.217 | 0.038-0.385 | 0.207 |
| 4 ECG Peak3 Max Amp | 0.352-1.874 | 1.095 | 0.539-1.893 | 1.202 | 0.760-2.036 | 1.384 | 0.679-1.900 | 1.277 |
| 5 ECG Peak2 Power σ | 0.537-1.434 | 0.975 | 0.356-1.155 | 0.747 | 0.294-1.045 | 0.661 | 0.290-1.022 | 0.649 |
| 6 Intercept | −99.339-−28.626 | −64.005 | −102.762-−39.088 | −70.684 | −92.111-−31.916 | −61.954 | −89.076-−30.567 | −59.896 |

TABLE 7

Range of coefficient values and recommended coefficient values for each parameter, based on data collection over a fixed time interval of about 55 minutes

| Parameter | up to 3 hours (range) | up to 3 hours | up to 6 hours (range) | up to 6 hours | up to 12 hours (range) | up to 12 hours | up to 24 hours (range) | up to 24 hours |
|---|---|---|---|---|---|---|---|---|
| 1 PPG Peak1 Maxpower | 0.217-1.372 | 0.795 | 0.419-1.431 | 0.923 | 0.282-1.225 | 0.754 | 0.332-1.241 | 0.787 |
| 2 PPG Peak2 $10^{th}$ percent | −0.311-−0.093 | −0.190 | −0.275-−0.069 | −0.164 | −0.278-−0.067 | −0.163 | −0.288-−0.072 | −0.168 |
| 3 PPG Max Med Amp | 0.028-0.536 | 0.274 | −0.026-0.395 | 0.178 | 0.029-0.418 | 0.218 | 0.012-0.382 | 0.192 |
| 4 ECG Peak3 Max Amp | 0.488-2.110 | 1.281 | 0.624-2.047 | 1.322 | 0.823-2.158 | 1.477 | 0.728-2.007 | 1.356 |
| 5 ECG Peak2 Power σ | 0.529-1.369 | 0.930 | 0.383-1.140 | 0.749 | 0.314-1.030 | 0.663 | 0.306-1.006 | 0.647 |
| 6 Intercept | −98.598-−26.379 | −62.632 | −101.418-−37.223 | −69.269 | −91.653-−30.937 | −61.418 | −90.292-−31.101 | −60.923 |

In an example embodiment, a plurality of additional predictions are determined, based on whether the caregiver will order a first massive blood transfusion (MT1) of at least 5 units of pRBC within 4 hours after the collection of the first data; whether the patient will require a second massive blood transfusion (MT2) of at least 10 units of pRBC within 6 hours after the collection of the first data; whether the patient will require a third massive blood transfusion (MT3) of at least 10 units of pRBC within 24 hours after the collection of the first data and whether the patient will die (Mortality). The MT1, MT2 MT3 and Mortality predictions are determined in a similar manner as the method for determining the prediction P with the data processing system 104, by applying one or more secondary coefficients for the MT1, MT2, MT3 and Mortality predictions to the values for the one or more parameters of the first data. The secondary coefficients for the MT1, MT2, MT3 and Mortality predictions are determined in a similar manner as the method for determining the coefficients for the prediction P of whether the caregiver will order a blood transfusion of one or more blood units. In other embodiments, predictions are determined based on whether the caregiver will order a massive blood transfusion of at least 3 units of pRBC within one hour after collection of the first data.

Table 8 provides a list of one or more parameters that are used to determine the MT1, MT2 and MT3 predictions in the method 200 of FIG. 2A, and a 95% confidence interval range of secondary coefficients for the parameters for each MT1, MT2 and MT3 prediction. Additionally, Table 8 also provides a list of the recommended secondary coefficient values within the coefficient interval ranges, for each parameter. Blank entries in Table 8 represent zero value secondary coefficients, and thus parameters that are not deemed useful in the model. The secondary coefficient ranges of the parameters listed in Table 8 are based on the first data collection over a fixed time interval of about 15 minutes. Table 9 is also provided, which lists the range of secondary coefficient values and the recommended secondary coefficient values for each parameter, based on the first data being collection over a fixed time interval of about 30 minutes. Similarly, Table 10 is also provided, which lists the range of secondary coefficient values and the recommended secondary coefficient values for each parameter, based on the first data being collection over a fixed time interval of about 60 minutes.

TABLE 8

Range of secondary coefficient values and recommended secondary coefficient values for each parameter including Patient Demographics, based on data collection over a fixed time interval of about 15 minutes

| Parameter | MT1 (range) | MT1 | MT2 (range) | MT2 | MT3 (range) | MT3 |
|---|---|---|---|---|---|---|
| 1 Age | −0.034-0.02 | −0.006 | −0.032-0.032 | 0.001 | −0.036-0.034 | −0.00001 |

TABLE 8-continued

Range of secondary coefficient values and recommended secondary coefficient values for each parameter including Patient Demographics, based on data collection over a fixed time interval of about 15 minutes

|    | Parameter | MT1 (range) | MT1 | MT2 (range) | MT2 | MT3 (range) | MT3 |
|----|-----------|-------------|-----|-------------|-----|-------------|-----|
| 2  | Sex | 0.035-2.56 | 1.17 | −0.784-2.07 | 0.495 | −0.522-2.471 | 0.804 |
| 3  | PreH-HR | | | 0.005-0.58 | 0.032 | 0.005-0.057 | 0.0307 |
| 4  | 10 percentile PPG | | | | | −0.015-0.0025 | −0.006 |
| 5  | 20 percentile PPG | −0.007-−0.001 | −0.004 | −0.035-−0.004 | −0.02 | | |
| 6  | 30 percentile PPG | | | −0.0015-0.027 | 0.013 | | |
| 7  | 40 percentile PPG | | | | | −0.037-0.009 | −0.0154 |
| 8  | 50 percentile PPG | | | | | −0.004-0.033 | 0.0161 |
| 9  | 60 percentile PPG | | | | | | |
| 10 | 70 percentile PPG | | | | | | |
| 11 | 80 percentile PPG | | | | | | |
| 12 | 90 percentile PPG | | | | | | |
| 13 | 25 percentile PPG | | | | | | |
| 14 | 75 percentile PPG | | | | | | |
| 15 | 25-75 percentile PPG | | | | | | |
| 16 | % time for SPO2 < 98% | | | | | | |
| 17 | Dose for SPO2 < 98% | | | | | | |
| 18 | % time for SPO2 < 95% | | | | | | |
| 19 | Dose for SPO2 < 95% | | | | | | |
| 20 | % time for SPO2 < 92% | | | | | | |
| 21 | Dose for SPO2 < 92% | −1.96-−0.142 | −0.88 | | | | |
| 22 | % time for SPO2 < 90% | | | | | | |
| 23 | Dose for SPO2 < 90% | | | | | | |
| 24 | % time for SPO2 < 86% | 13.76-−48.75 | 28.62 | | | 1.894-−11.48 | 7.042 |
| 25 | Dose for SPO2 < 86% | | | | | | |
| 26 | 25 percentile SPO2 | | | | | | |
| 27 | 50 percentile SPO2 | 0.513-4.56 | 2.54 | | | | |
| 28 | 75 percentile SPO2 | | | −0.207-5.382 | 2.893 | 1.17-6.094 | 3.762 |
| 29 | mean SP02 | | | | | | |
| 30 | % time for HR > 120 | | | | | | |
| 31 | Dose for HR > 120 | | | | | | |
| 32 | % time for HR > 110 | | | | | | |
| 33 | Dose for HR > 110 | | | | | | |
| 34 | % time for HR > 100 | | | | | | |
| 35 | Dose for HR > 100 | | | | | | |
| 36 | % time for HR < 72 | | | | | | |
| 37 | Dose for HR < 72 | 0.341-1.221 | 0.731 | | | −0.0068-0.5462 | 0.2697 |
| 38 | % time for HR < 60 | | | | | | |

TABLE 8-continued

Range of secondary coefficient values and recommended secondary coefficient values for each parameter including Patient Demographics, based on data collection over a fixed time interval of about 15 minutes

| | Parameter | MT1 (range) | MT1 | MT2 (range) | MT2 | MT3 (range) | MT3 |
|---|---|---|---|---|---|---|---|
| 39 | Dose for HR < 60 | | | | | | |
| 40 | 25 percentile HR | 0.064-0.272 | 0.142 | | | | |
| 41 | 50 percentile HR | −0.22-−0.03 | −0.10 | | | | |
| 42 | 75 percentile HR | | | | | | |
| 43 | mean HR | | | | | | |
| 44 | Intercept | −130.1-−39.55 | 79.69 | −10.46-−2.25 | 6.127 | −63.43-−6.181 | −34.56 |
| 45 | Thresholds Range | 0.5-1.0 | 0.5 | 0.5-1.0 | 0.5 | 0.5-1.0 | 0.5 |

TABLE 9

Range of secondary coefficient values and recommended secondary coefficient values for each parameter including Patient Demographics, based on data collection over a fixed time interval of about 30 minutes

| | Parameter | MT1 (range) | MT1 | MT2 (range) | MT2 | MT3 (range) | MT3 |
|---|---|---|---|---|---|---|---|
| 1 | Age | −0.040-0.015 | −0.011 | −0.035-0.030 | −0.0014 | −0.026-0.0344 | 0.0051 |
| 2 | Sex | −0.155-2.349 | 0.982 | −0.915-2.081 | 0.438 | −0.665-2.241 | 0.633 |
| 3 | PreH-HR | | | 0.0009-0.0053 | 0.0262 | 0.002-0.051 | 0.026 |
| 4 | 10 percentile PPG | | | | | | |
| 5 | 20 percentile PPG | | | | | | |
| 6 | 30 percentile PPG | | | | | | |
| 7 | 40 percentile PPG | | | | | | |
| 8 | 50 percentile PPG | | | | | | |
| 9 | 60 percentile PPG | | | 0.0013-0.011 | 0.0063 | 0.0017-0.011 | 0.0064 |
| 10 | 70 percentile PPG | | | | | | |
| 11 | 80 percentile PPG | | | | | | |
| 12 | 90 percentile PPG | −0.0084-−0.0031 | −0.0057 | | | | |
| 13 | 25 percentile PPG | | | −0.0199-−0.0073 | −0.013 | −0.018-−0.0069 | −0.012 |
| 14 | 75 percentile PPG | | | | | | |
| 15 | 25-75 percentile PPG | 0.0047-0.0137 | 0.009 | | | | |
| 16 | % time for SPO2 < 98% | | | | | | |
| 17 | Dose for SPO2 < 98% | −1.10-−0.096 | −0.525 | | | | |
| 18 | % time for SPO2 < 95% | | | | | | |
| 19 | Dose for SPO2 < 95% | | | | | | |
| 20 | % time for SPO2 < 92% | | | | | | |
| 21 | Dose for SPO2 < 92% | | | | | | |
| 22 | % time for SPO2 < 90% | | | | | | |
| 23 | Dose for SPO2 < 90% | | | | | | |
| 24 | % time for SPO2 < 86% | 13.07-45.279 | 27.434 | | | | |
| 25 | Dose for SPO2 < 86% | | | | | | |

TABLE 9-continued

Range of secondary coefficient values and recommended secondary coefficient values for each parameter including Patient Demographics, based on data collection over a fixed time interval of about 30 minutes

|    | Parameter              | MT1 (range)        | MT1    | MT2 (range)         | MT2    | MT3 (range)         | MT3    |
|----|------------------------|--------------------|--------|---------------------|--------|---------------------|--------|
| 26 | 25 percentile SPO2     |                    |        |                     |        |                     |        |
| 27 | 50 percentile SPO2     | −0.258-2.837       | 1.355  |                     |        |                     |        |
| 28 | 75 percentile SPO2     |                    |        |                     |        | −0.0943-5.470       | 3.032  |
| 29 | mean SP02              |                    |        |                     |        |                     |        |
| 30 | % time for HR > 120    |                    |        | 0.017-0.127         | 0.0735 | 0.0216-0.125        | 0.0753 |
| 31 | Dose for HR > 120      |                    |        |                     |        |                     |        |
| 32 | % time for HR > 110    | 0.0295-0.109       | 0.069  |                     |        |                     |        |
| 33 | Dose for HR > 110      |                    |        |                     |        |                     |        |
| 34 | % time for HR > 100    |                    |        | −0.0782-0.231       | 0.106  |                     |        |
| 35 | Dose for HR > 100      |                    |        |                     |        |                     |        |
| 36 | % time for HR < 72     |                    |        |                     |        |                     |        |
| 37 | Dose for HR < 72       | 0.274-1.064        | 0.641  |                     |        |                     |        |
| 38 | % time for HR < 60     |                    |        |                     |        |                     |        |
| 39 | Dose for HR < 60       |                    |        |                     |        |                     |        |
| 40 | 25 percentile HR       |                    |        |                     |        |                     |        |
| 41 | 50 percentile HR       |                    |        |                     |        |                     |        |
| 42 | 75 percentile HR       |                    |        |                     |        |                     |        |
| 43 | mean HR                |                    |        |                     |        |                     |        |
| 44 | Intercept              | −108.86-−28.92     | −66.10 | −10.15-−1.54        | −5.60  | −10.65-−2.383       | −6.272 |
| 45 | Thresholds Range       | 0.5-1.0            | 0.5    | 0.5-1.0             | 0.5    | 0.5-1.0             | 0.5    |

TABLE 10

Range of secondary coefficient values and recommended secondary coefficient values for each parameter including Patient Demographics, based on data collection over a fixed time interval of about 60 minutes

|    | Parameter         | MT1 (range)     | MT1    | MT2 (range)       | MT2    | MT3 (range)       | MT3     |
|----|-------------------|-----------------|--------|-------------------|--------|-------------------|---------|
| 1  | Age               | −0.039-−0.013   | −0.012 | −0.023-−0.045     | 0.012  | −0.039-−0.0264    | −0.005  |
| 2  | Sex               | −0.495-−1.803   | 0.573  | −0.927-−2.243     | 0.528  | −0.759-−2.205     | 0.580   |
| 3  | PreH-HR           |                 |        |                   |        |                   |         |
| 4  | 10 percentile PPG |                 |        |                   |        |                   |         |
| 5  | 20 percentile PPG | −0.056-0.0011   | −0.029 |                   |        |                   |         |
| 6  | 30 percentile PPG |                 |        | −0.0217-−0.0039   | −0.013 | −0.016-−0.0021    | −0.0093 |
| 7  | 40 percentile PPG |                 |        |                   |        |                   |         |
| 8  | 50 percentile PPG |                 |        | −0.0011-−0.0148   | 0.0073 | −0.0018-−0.011    | 0.0048  |
| 9  | 60 percentile PPG |                 |        |                   |        |                   |         |
| 10 | 70 percentile PPG |                 |        |                   |        |                   |         |
| 11 | 80 percentile PPG |                 |        |                   |        |                   |         |
| 12 | 90 percentile PPG |                 |        |                   |        |                   |         |

TABLE 10-continued

Range of secondary coefficient values and recommended secondary coefficient values for each parameter including Patient Demographics, based on data collection over a fixed time interval of about 60 minutes

| | Parameter | MT1 (range) | MT1 | MT2 (range) | MT2 | MT3 (range) | MT3 |
|---|---|---|---|---|---|---|---|
| 13 | 25 percentile PPG | −0.0046−−0.0469 | 0.0217 | | | | |
| 14 | 75 percentile PPG | | | | | | |
| 15 | 25-75 percentile PPG | | | | | | |
| 16 | % time for SPO2 < 98% | | | | | | |
| 17 | Dose for SPO2 < 98% | | | | | | |
| 18 | % time for SPO2 < 95% | | | −59.214−−7.71 | −29.07 | | |
| 19 | Dose for SPO2 < 95% | −1.382−−0.146 | −0.754 | | | | |
| 20 | % time for SPO2 < 92% | | | 22.26−−146.45 | 83.05 | | |
| 21 | Dose for SPO2 < 92% | | | | | −1.321−−0.0002 | −0.654 |
| 22 | % time for SPO2 < 90% | | | −183.31−−9.063 | −97.87 | | |
| 23 | Dose for SPO2 < 90% | | | | | | |
| 24 | % time for SPO2 < 86% | 17.981−−56.242 | 36.429 | 15.314−−127.45 | 68.18 | 16.317−−55.133 | 34.752 |
| 25 | Dose for SPO2 < 86% | | | | | | |
| 26 | 25 percentile SPO2 | | | | | | |
| 27 | 50 percentile SPO2 | −0.426−−2.741 | 1.235 | | | | |
| 28 | 75 percentile SPO2 | | | | | | |
| 29 | mean SP02 | | | | | | |
| 30 | % time for HR > 120 | | | | | | |
| 31 | Dose for HR > 120 | | | | | | |
| 32 | % time for HR > 110 | 0.047−−0.131 | 0.088 | 0.0428−−0.1532 | 0.0957 | 0.053−−0.150 | 0.1003 |
| 33 | Dose for HR > 110 | | | | | | |
| 34 | % time for HR > 100 | | | | | −0.077−−0.199 | 0.0864 |
| 35 | Dose for HR > 100 | 0.324−−0.943 | 0.611 | | | 0.356−−1.137 | 0.702 |
| 36 | % time for HR < 72 | | | | | | |
| 37 | Dose for HR < 72 | | | 0.9334−−5.01 | 2.396 | | |
| 38 | % time for HR < 60 | | | | | | |
| 39 | Dosefor HR < 60 | | | | | | |
| 40 | 25 percentile HR | | | | | | |
| 41 | 50 percentile HR | | | | | | |
| 42 | 75 percentile HR | | | | | | |
| 43 | mean HR | | | | | | |
| 44 | Intercept | −96.27−−33.90 | −62.87 | −504.37−−95.98 | −242.82 | −117.34−−38.62 | −73.65 |
| 45 | Thresholds Range | 0.5-1.0 | 0.5 | 0.5-1.0 | 0.5 | 0.5-1.0 | 0.5 |

Table 11 provides a list of one or more parameters that are used to determine the MT1, MT2, MT3 and Mortality predictions in the method 250 of FIG. 2B, and a 95% confidence interval range of secondary coefficients for the parameters for each MT1, MT2, MT3 and Mortality prediction. Additionally, Table 11 also provides a list of the recommended secondary coefficient values within the coefficient interval ranges, for each parameter. The secondary coefficient ranges of the parameters listed in Table 11 are based on the first data collection over a fixed time interval of about 5 minutes. Table 12 is also provided, which lists the range of secondary coefficient values and the recommended secondary coefficient values for each parameter, based on the first data collection over a fixed time interval of about 15 minutes. Table 13 is also provided, which lists the range of secondary coefficient values and the recommended secondary coefficient values for each parameter, based on the first data collection over a fixed time interval of about 30 minutes. Similarly, Table 14 is also provided, which lists the range of secondary coefficient values and the recommended secondary coefficient values for each parameter, based on the first data collection over a fixed time interval of about 55 minutes. In other embodiments, a first fixed time interval is selected in a range from about 1 minute to about 10 minutes, a second fixed time interval is selected in a range from about 5 minutes to about 25 minutes, a third fixed time interval is selected in a range from about 15 minutes to about 45 minutes and a fourth fixed time interval is selected in a range from about 40 minutes to about 70 minutes. In some embodiments, selecting a value of the fixed time interval near a lower end of the above ranges advantageously provides a more immediate prediction whether the caregiver will order the blood transfusion. In other embodiments, selecting a value of the fixed time interval near an upper end of the above ranges advantageously provides a more accurate prediction whether the caregiver will order the blood transfusion.

TABLE 11

Range of secondary coefficient values and recommended secondary coefficient values for each parameter, based on data collection over a fixed time interval of about 5 minutes

| Parameter | Mortality (range) | Mortality | MT1 (range) | MT1 | MT2 (range) | MT2 | MT3 (range) | MT3 |
|---|---|---|---|---|---|---|---|---|
| 1 PPG Peak1 Max power | 0.290-1.111 | 0.559 | 0.480-1.164 | 0.755 | 0.445-1.716 | 0.842 | 0.461-1.731 | 0.893 |
| 2 PPG Peak 2 $10^{th}$ percent | −0.706-−0.176 | −0.475 | −0.967-−0.440 | −0.699 | −1.050-−0.291 | −0.722 | −0.979-−0.216 | −0.637 |
| 3 PPG Max Med Amp | −0.057-0.032 | −0.022 | −0.054-0.064 | −0.015 | −0.079-0.034 | −0.036 | −0.078-0.035 | −0.034 |
| 4 ECG Peak3 Max Amp | −0.143-0.429 | 0.054 | −0.172-0.386 | 0.024 | −0.285-0.253 | −0.087 | −0.247-0.319 | −0.046 |
| 5 ECG Peak2 Power σ | −0.227-0.688 | 0.256 | −0.400-0.642 | 0.166 | −0.268-0.885 | 0.348 | −0.388-0.776 | 0.255 |
| 6 Intercept | −50.963-1.811 | −6.274 | −28.361-2.155 | −3.585 | −77.273-2.675 | −6.650 | −83.788-3.131 | −15.525 |

TABLE 12

Range of secondary coefficient values and recommended secondary coefficient values for each parameter, based on data collection over a fixed time interval of about 15 minutes

| Parameter | Mortality (range) | Mortality | MT1 (range) | MT1 | MT2 (range) | MT2 | MT3 (range) | MT3 |
|---|---|---|---|---|---|---|---|---|
| 1 PPG Peak1 Maxpower | 0.046-1.203 | 0.549 | 0.187-1.242 | 0.512 | 0.254-2.033 | 1.030 | 0.218-1.877 | 0.943 |
| 2 PPG Peak 2 $10^{th}$ percent | −0.456-−0.036 | −0.226 | −0.543-−0.089 | −0.283 | −0.501-−0.057 | −0.260 | −0.462-−0.023 | −0.224 |
| 3 PPG Max Med Amp | −0.111-0.328 | 0.099 | 0.158-0.763 | 0.450 | 0.220-1.144 | 0.661 | 0.260-1.097 | 0.660 |
| 4 ECG Peak3 Max Amp | 0.404-2.097 | 1.233 | −0.111-1.780 | 0.809 | −0.085-2.492 | 1.148 | 0.274-2.746 | 1.458 |
| 5 ECG Peak2 Power σ | 0.215-1.189 | 0.683 | 0.219-1.341 | 0.752 | 0.251-1.707 | 0.917 | 0.158-1.506 | 0.776 |
| 6 Intercept | −83.893-−7.887 | −39.053 | −89.023-−14.558 | −39.111 | −150.855-−18.293 | −83.428 | −146.600-−21.909 | −83.410 |

TABLE 13

Range of secondary coefficient values and recommended secondary coefficient values for each parameter, based on data collection over a fixed time interval of about 30 minutes

| Parameter | Mortality (range) | Mortality | MT1 (range) | MT1 | MT2 (range) | MT2 | MT3 (range) | MT3 |
|---|---|---|---|---|---|---|---|---|
| 1 PPG Peak1 Max power | 0.182-1.215 | 0.569 | −0.090-1.377 | 0.642 | 0.443-2.685 | 1.510 | 0.243-2.254 | 1.219 |
| 2 PPG Peak 2 $10^{th}$ percent | −0.222-0.013 | −0.115 | −0.313-−0.088 | −0.197 | −0.390-−0.125 | −0.257 | −0.359-−0.100 | −0.231 |
| 3 PPG Max Med Amp | −0.127-0.350 | 0.104 | 0.205-0.900 | 0.540 | 0.083-1.173 | 0.603 | 0.165-1.135 | 0.630 |

TABLE 13-continued

Range of secondary coefficient values and recommended secondary coefficient values for each parameter, based on data collection over a fixed time interval of about 30 minutes

| Parameter | Mortality (range) | Mortality | MT1 (range) | MT1 | MT2 (range) | MT2 | MT3 (range) | MT3 |
|---|---|---|---|---|---|---|---|---|
| 4 ECG Peak3 Max Amp | 0.679-2.411 | 1.525 | 0.072-2.065 | 1.034 | 0.289-3.185 | 1.626 | 0.666-3.473 | 1.969 |
| 5 ECG Peak2 Power σ | 0.241-1.064 | 0.638 | 0.446-1.546 | 0.967 | 0.523-1.997 | 1.175 | 0.404-1.732 | 1.006 |
| 6 Intercept | −92.003-−17.137 | −51.093 | −103.862-−14.132 | −58.541 | −192.512-−53.541 | −117.971 | −171.979-−46.500 | −105.666 |

TABLE 14

Range of secondary coefficient values and recommended secondary coefficient values for each parameter, based on data collection over a fixed time interval of about 55 minutes

| Parameter | Mortality (range) | Mortality | MT1 (range) | MT1 | MT2 (range) | MT2 | MT3 (range) | MT3 |
|---|---|---|---|---|---|---|---|---|
| 1 PPG Peak1 Max power | 0.149-1.445 | 0.798 | −0.079-1.453 | 0.685 | 0.641-3.023 | 1.745 | 0.382-2.451 | 1.368 |
| 2 PPG Peak 2 $10^{th}$ percent | −0.219-−0.011 | −0.121 | −0.317-−0.103 | −0.207 | −0.371-−0.099 | −0.234 | −0.316-−0.062 | −0.191 |
| 3 PPG Max Med Amp | −0.105-0.425 | 0.149 | 0.349-1.141 | 0.732 | 0.379-1.685 | 0.991 | 0.381-1.501 | 0.912 |
| 4 ECG Peak3 Max Amp | 0.666-2.480 | 1.551 | 0.308-2.489 | 1.354 | 0.277-3.452 | 1.745 | 0.697-3.705 | 2.094 |
| 5 ECG Peak2 Power σ | 0.261-1.066 | 0.658 | 0.566-1.630 | 1.089 | 0.812-2.445 | 1.552 | 0.619-2.018 | 1.276 |
| 6 Intercept | −107.073-−26.884 | −66.522 | −117.647-−23.854 | −70.240 | −232.099-−78.278 | −147.956 | −199.373-−66.033 | −128.031 |

According to an example embodiment of the method of FIG. 3A, the data processing system 104 obtained data for values of one or more parameters of a characteristic of the continuous PPG waveform during treatment of a plurality of patients. In an example embodiment, a shock index (SI) of at least 0.60 was used to include patients with a higher probability of requiring a transfusion. The SI is defined as a ratio of the heart rate (in beats per minute) to the systolic blood pressure (in millimeters of mercury). In an example embodiment, the study was conducted in which 556 trauma patients were enrolled, 37 of those patients received a transfusion within 24 hours, and the data for the parameters listed in Table 1 was obtained for all of the patients over a 24 hour period of treatment. The pulse oximeter 102 was used to measure PPG waveform data including heart rate, oxygen saturation and PPG amplitude data over the fixed time periods, such as 15 minutes, 30 minutes and 60 minutes, for example. The data processing system 104 received the data from the pulse oximeter 102, including the parameters listed in Table 1.

According to an example embodiment of the method of FIG. 3B, the data processing system 104 obtained data for values of one or more parameters of a peak characteristic of the Fourier transform of the continuous PPG waveform and/or ECG waveform during treatment of a plurality of patients. In an example embodiment, adult patients of an age of 18 years or older and with a shock index (SI) of at least 0.62 was used to qualify trauma patients for a study. In an example embodiment, the study was conducted in which 897 trauma patients (614 male, 283 female) were enrolled in the study. Table 19 below summarizes the demographic characteristics of this group of patients. In this example embodiment, a majority of injuries in the group were blunt (81.6%) followed by penetrating injuries (13.0%).

TABLE 19

Demographic characteristics of enrolled patients (N = 897)

| Characteristic | Value |
|---|---|
| Mean age, yr (SD) | 40.4 (17.8) |
| Admission Glasgow Coma Scale score | min: 3; max: 15 |
| Injury Severity Score ($1^{st}$, $2^{nd}$, $3^{rd}$ quartiles) | 4.0, 5.5, 14.0 |
| Sex, n (%) | |
| Male | 614 (68.5) |
| Female | 283 (31.5) |
| Injury type, n (%) | |
| Blunt | 732 (81.6) |
| Penetrating | 117 (13.0) |
| Other | 48 (5.4) |
| Mechanism of injury, n (%) | |
| Motor vehicle associated | 421 (46.9) |
| Falls | 198 (22.1) |
| Assault (non GSW) | 122 (13.6) |
| GSW | 40 (4.5) |
| Other | 116 (12.9) |

SD = standard deviation.

In the example embodiment, 71 of those patients received a transfusion within 12 hours, and the data for the parameters of a peak characteristic of the continuous PPG waveform and ECG waveform was obtained for the patients over a 24 hour period of treatment. Table 15 below shows a proportion of blood transfusions given at different time intervals to the patients.

TABLE 15

Proportion of blood transfusion at different time intervals (N = 897)

| | 1-3 hour | 1-6 hour | 1-12 hour | MT1 | MT2 | MT3 |
|---|---|---|---|---|---|---|
| Use blood | 46 | 60 | 71 | 26 | 15 | 17 |

The data processing system 104 assigned a respective result for each patient based on whether the patient received a blood transfusion within the time ranges of 3 hours, 6 hours, 12 hours and 24 hours after the commencement of the collection of the PPG waveform data. In an example embodiment, the processor 104 assigned the result a value of 1.0 if a patient did receive a transfusion in a time range of treatment and assigned the result a value of 0 if the patient did not receive a transfusion during the time range of treatment. In an example embodiment, for each time range, the data processing system 104 fitted the data for the values of the one or more parameters to the results for the patients, using a software package such as MatLab® 3.13 R2011B; MathWorks, Natick, Mass. Based on the fitting of the data for the values of the one or more parameters to the results for the patients, the data processing system 104 determined the coefficients (see Table 1) for the one or more parameters, for each time range, to determine a model for predicting whether a caregiver will order a blood transfusion within each time range, based on an input of the one or more parameters. Additional statistical analysis and evaluation was implemented with R software version 3.1.1; R Development Core Team, Vienna, Austria and SAS 9.3 PROC LOGISTIC, SAS Institute, Cary N.C.

To measure the performance of the prediction model, a true positive rate (TPR) is calculated, based on a ratio of the number of cases where a transfusion was ordered and whose prediction (P) value exceeded the threshold to the total number of cases whose prediction (P) value exceeded the threshold. Additionally, a false positive rate (FPR) is calculated, which is based on a ratio of the number of cases where a transfusion was not ordered and had a prediction value (P) that exceeded the transfusion threshold to the total number of cases where the prediction (P) value exceeded the transfusion threshold. The TPR and the FPR varies, based on the numerical threshold. FIG. 3C illustrates an example of a receiver operating characteristic (ROC) curve 320, which plots the TPR 322 versus the FPR 324, for a range of transfusion thresholds. As appreciated by one skilled in the art, an area under the ROC curve (AUROC) provides a measure of the performance of the prediction model, where the larger the area (up to 1), the better the performance of the model at predicting whether a transfusion should be ordered. In an example embodiment, the AUROC for the models for predicting whether the blood transfusion should be ordered within 3 hours, 6 hours, 12 hours and 24 hours of the data collection is in a range of 0.80-0.84, in excess of conventional prediction methods based on conventional vital sign (VS) data collection of parameters other than the parameters listed in Table 1. As illustrated in FIG. 3C, a first ROC curve 326 is based on the first data collection over the fixed time interval of 15 minutes and the second ROC curve 328 is based on the first data collection over the fixed time interval of 30 minutes. In an example embodiment, the performance of the prediction model of whether to order the blood transfusion within each time range based on the fixed time interval of 15 minutes of data (AUROC 0.80-0.83) was unexpectedly insignificant to the performance of the prediction model of whether to order the blood transfusion within each time range based on a longer fixed time interval of 30 minutes (AUROC 0.81-0.85) or 60 minutes (0.82-0.85) of data collection.

FIG. 6A is a graph that illustrates an example of a plot 610 of AUROC for a model using PPG waveform data versus data collection time of the PPG waveform data, according to one embodiment. The horizontal axis 602 is time in units of seconds (sec) and the vertical axis 604 is area under the ROC curve (AUROC). The plot 610 includes a training model plot 612 and a testing model plot 614, where the training model plot 612 is based on a model that considers a frequency of parameters of the peak characteristic of the spectrogram 500 of the PPG waveform 414 among the patients in the study. As shown in the plot 610, the AUROC for the model using only PPG waveform data increases with the data collection time of the PPG waveform data and approaches a maximum value of approximately 0.80 for data collection times greater than 50 minutes.

FIG. 6B illustrates an example of a plot 620 of AUROC for a model using ECG waveform data versus data collection time of the ECG waveform data, according to one embodiment. The horizontal axis 602 is time in units of seconds (sec) and the vertical axis 604 is area under the ROC curve (AUROC). The plot 620 includes a training model plot 622 and a testing model plot 624, where the training model plot 622 is based on a model that considers a frequency of parameters of the peak characteristic of the spectrogram of the ECG waveform 150 among the patients in the study. As shown in the plot 620, the AUROC for the model using only ECG waveform data increases with the data collection time of the ECG waveform data and approaches a maximum value of 0.85 at a data collection time of approximately 40 minutes.

FIG. 6C illustrates an example of a plot 630 of AUROC for a model using combined PPG and ECG waveform data versus data collection time of the PPG and ECG waveform data, according to one embodiment. The horizontal axis 602 is time in units of seconds (sec) and the vertical axis 604 is area under the ROC curve (AUROC). The plot 630 includes a training model plot 632 and a testing model plot 634, where the training model plot 632 is based on a model that considers a frequency of parameters of the peak characteristic of the spectrogram 500 of the PPG waveform 414 and the peak characteristic of the spectrogram of the ECG waveform 150 among the patients in the study. As shown in the plot 630, the AUROC for the model using PPG and ECG waveform data increases with the data collection time of the PPG and ECG waveform data and approaches a maximum value of approximately 0.90 for data collection times greater than 35 minutes. Thus, the model using combined PPG and ECG waveform data is more accurate than models using either one of the PPG or ECG waveform data. Tables 16, 17 and 18 below summarize the average AUROC of the logistic regression models and their 95% confidence intervals (CI), using a data collection time of 15 minutes for ECG and/or PPG waveform data. Table 16 depicts the AUROC for a model using pre-hospital vital signs collected at the scene of injury, and the AUROC ranges from 0.70 to 0.76. Table 17 depicts the AUROC for a model using ECG or PPG waveform data collected over 15 minutes and the AUROC improves to 0.74-0.88 compared to the AUROC using pre-hospital vital signs. Table 18 depicts the AUROC for a model using combined ECG and PPG waveform data, and the AUROC improves to 0.80-0.94.

TABLE 16

Performance evaluation of prediction using prehospital vital signs

|  | ROC | 95% CI | Sensitivity | Specificity |
|---|---|---|---|---|
| 1-3 hr | 0.76 | 0.67-0.85 | 0.60 | 0.91 |
| 1-6 hr | 0.72 | 0.64-0.80 | 0.49 | 0.91 |
| 1-12 hr | 0.70 | 0.63-0.78 | 0.52 | 0.87 |
| MT1 | 0.73 | 0.59-0.87 | 0.61 | 0.87 |
| MT2 | 0.75 | 0.56-0.94 | 0.62 | 0.87 |
| MT3 | 0.74 | 0.56-0.92 | 0.57 | 0.86 |

TABLE 17

Performance evaluations of prediction using ECG or PPG data collected over 15 minutes

|  | PPG only | | | | ECG only | | | |
|---|---|---|---|---|---|---|---|---|
|  | ROC | 95% CI | Sensitivity | Specificity | ROC | 95% CI | Sensitivity | Specificity |
| 1-3 hr | 0.77 | 0.69-0.85 | 0.74 | 0.71 | 0.72 | 0.64-0.81 | 0.61 | 0.77 |
| 1-6 hr | 0.76 | 0.69-0.83 | 0.73 | 0.73 | 0.69 | 0.61-0.77 | 0.58 | 0.77 |
| 1-12 hr | 0.74 | 0.67-0.80 | 0.70 | 0.68 | 0.70 | 0.62-0.77 | 0.51 | 0.82 |
| MT1 | 0.82 | 0.71-0.92 | 0.73 | 0.84 | 0.74 | 0.63-0.86 | 0.69 | 0.77 |
| MT2 | 0.88 | 0.78-0.99 | 0.73 | 0.91 | 0.82 | 0.69-0.95 | 0.87 | 0.74 |
| MT3 | 0.88 | 0.79-0.97 | 0.94 | 0.70 | 0.82 | 0.71-0.94 | 0.88 | 0.71 |

TABLE 18

Performance evaluations of prediction using combined ECG and PPG data collected over 15 minutes

|  | ROC | 95% CI | Sensitivity | Specificity |
|---|---|---|---|---|
| 1-3 hr | 0.82 | 0.76-0.88 | 0.65 | 0.85 |
| 1-6 hr | 0.80 | 0.74-0.86 | 0.75 | 0.71 |
| 1-12 hr | 0.79 | 0.74-0.85 | 0.61 | 0.84 |
| MT1 | 0.87 | 0.79-0.95 | 0.77 | 0.88 |
| MT2 | 0.94 | 0.89-0.99 | 0.93 | 0.86 |
| MT3 | 0.94 | 0.90-0.98 | 0.94 | 0.83 |

Figure 7:
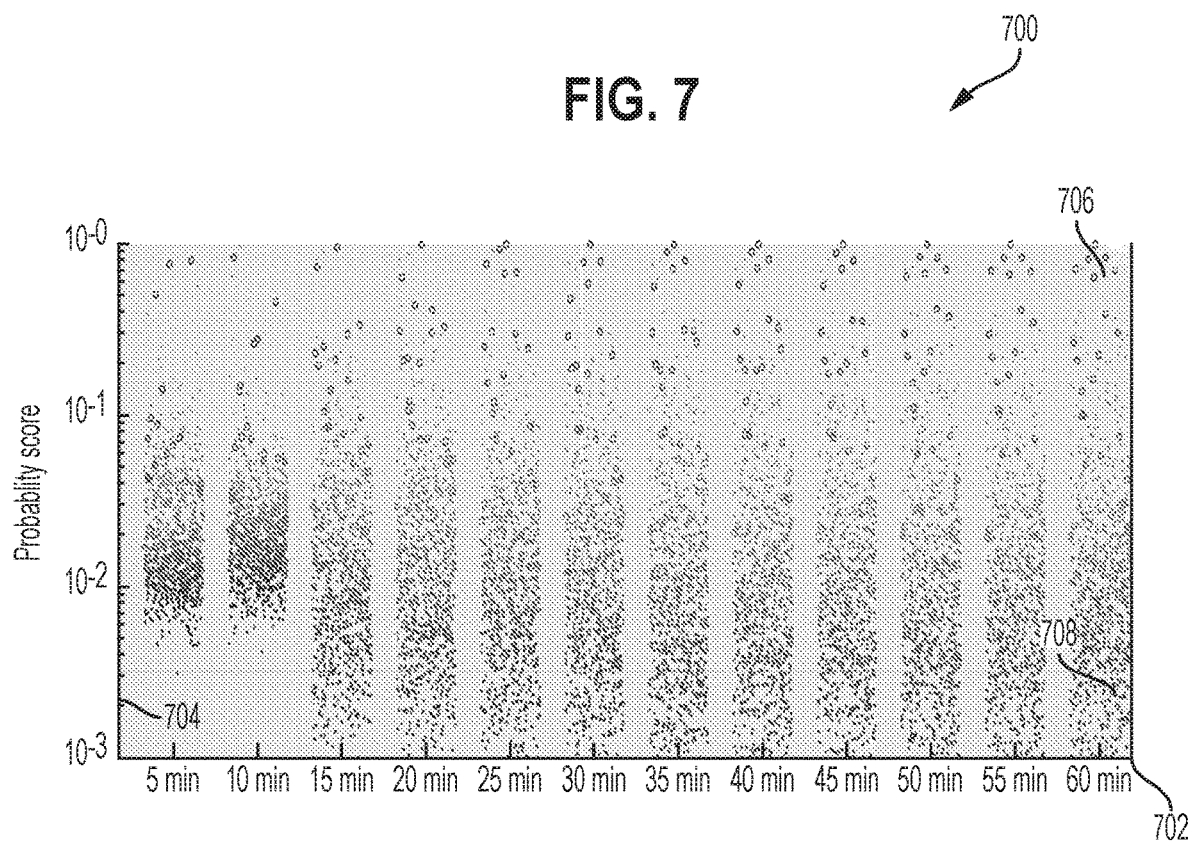
FIG. 7 is a graph that illustrates an example of a plot of a prediction value for true positive cases and true negative cases versus data collection time, according to one embodiment.

FIG. 7 is a graph that illustrates an example of a plot 700 of a prediction value for true positive cases and true negative cases versus data collection time, according to one embodiment. The horizontal axis 702 is data collection time, in units of minutes (min) and the vertical axis 704 is prediction score (unitless, between 0 and 1). True positive cases 706 (open circles) and true negative cases 708 (dots) are also depicted in the plot 700. As shown in FIG. 7, as the data collection time increases along axis 702 from 5 minutes to 55 minutes, a separation in the prediction score 704 between the true positive cases 706 and true negative cases 708 is greater and thus the model accuracy increases with data collection time.

Figure 8:
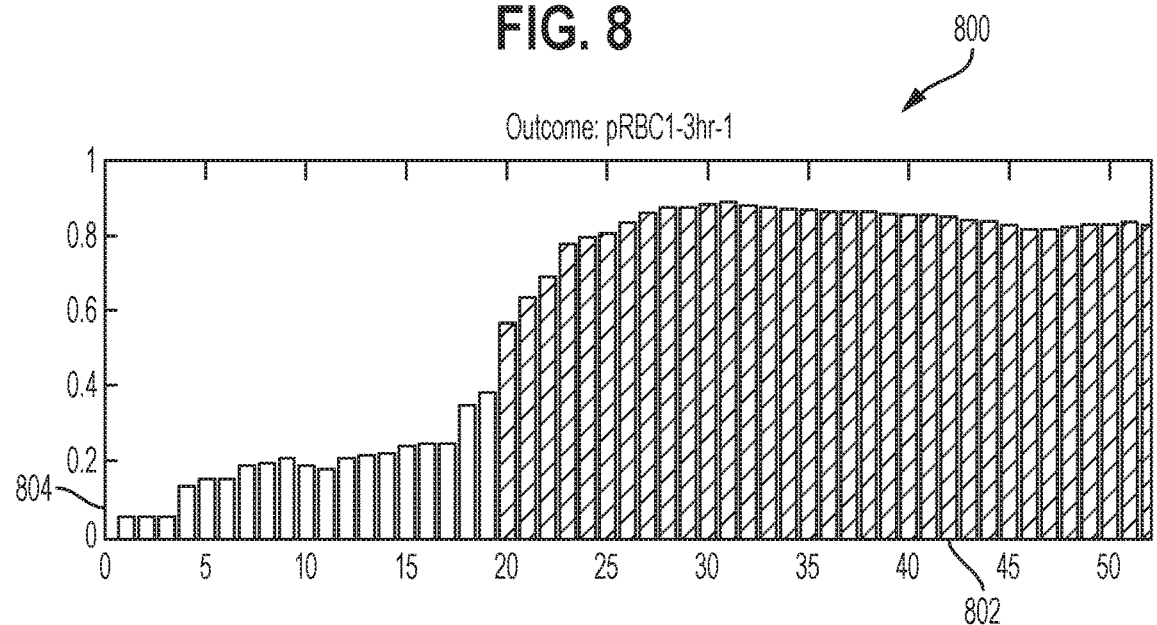
FIG. 8 is a graph that illustrates an example of a plot of a prediction value for a true positive case versus data collection time, according to one embodiment.

FIG. 8 is a graph that illustrates an example of a plot 800 of a prediction value of a true positive case versus data collection time, according to one embodiment. The horizontal axis 802 is data collection time, in units of minutes (min) and the vertical axis 804 is prediction score (unitless, between 0 and 1). As shown in the plot 800, as the data collection time increases from 1 minute to 25 minutes, the prediction score increases and thus a more accurate prediction is computed of the true positive case where a transfusion should be ordered. In an example embodiment, the prediction score is low (e.g. less than about 0.2), for times less than about 11 minutes; intermediate (e.g. prediction values between about 0.2 and about-0.5) for times from 11 minutes to about 19 minutes; and high (e.g. prediction values greater than about 0.5) at times greater than 20 minutes, leveling off at values above about 0.8 at times more than 25 minutes. In an example embodiment, blood units are ordered if the model predicts a probability for use of blood units and the prediction score is greater than about 0.5.

In an example embodiment, for each of the plurality of patients, continuous vital sign (VS) data is collected from each patient via. Bedmaster® software (Excel Medical Electronics, Jupiter Fla., USA) from networked patient monitors (GE-Marquette Solar 7000/8000, GE® Healthcare) using two VS data collection servers, as discussed in P. F. Hu, S. Yang, H. Li, L. G. Stansbury, F. Yang, G Hagegeorge, C. Miller, P. Rock, D. M. Stein, C. F. Mackenzie, *Reliable Collection of Real-time Patient Physiologic Data from Less Reliable Networks: a "monitor of monitors" system (MoMs), Journal of Medical Systems*, (2017)41: 3. In an example embodiment, electrocardiogram (ECG) and PPG waveforms were collected at 240 Hz. Heart rate (HR) values (from PPG) and oxygen saturation ($SpO_2$) values were obtained every five seconds (0.2 Hz) from the pulse oximeter 102. The collected data was compressed and transferred to the data processing system 104, such as through an intranet of the hospital facility, for example. In an example embodiment, VS data streaming rate after compression averaged 12 MB/hour for waveforms and 76 Kb/hour for VS data. One hour of continuous VS data and PPG waveform data was collected for analysis, beginning at the time of arrival of the patient at the trauma unit of the hospital. In an example embodiment, blood use was tracked by direct observation of resuscitation and by cross-validation with blood bank records tracking individual blood product unit types and time of release from the blood bank.

The pulse oximeter 102 was used to measure PPG waveform data, the electrodes 106 were used to measure ECG waveform data, and the data processing system 104 received the PPG waveform data and/or ECG waveform data, to determine the first data that indicates the peak characteristics of the Fourier transforms of the PPG waveform and ECG waveform. In an example embodiment, continuous vital signs (VS) data, 5-lead electrocardiogram (ECG) and finger photoplethysmograph (PPG) waveforms (240 Hz) were collected via BedMaster® (GE Marquette, Milwaukee, Wis.) vital signs collection system during the first two hours of resuscitation. In this example embodiment, both of the PPG and ECG waveforms were generated with a 12-bit analog-to-digital converter, giving the amplitude reading range from −2047 to 2048. In pre-processing, amplitude values outside of this range were filtered out by flagging them as not-a-number (NAN). In an example embodiment, the data processing system 104 receives data of the Fourier transforms of the PPG waveform and/or ECG waveform and determines the peak characteristics of the Fourier transforms. The data processing system 104 determines the parameter values for the peak characteristics, including frequency, amplitude and power over the fixed time periods, such as 15 minutes, 30 minutes and 60 minutes, for example.

In an example embodiment, the prediction models can run in real-time. Due to the simplicity of determining a Fourier transform, as well as fast and mature calculation algorithms, designed features of the prediction models can be efficiently calculated on mainstream computers. In an example embodiment, for one hour continuous 240 Hz PPG waveform, the set of STFT features can be calculated in less than 1 second, on a 64-bit Windows 7 machine with Core i5 2.67 GHz CPU and MATLAB® 3.13 R2011B; MathWorks, Natick, Mass. Since the predictive model only uses a subset of the calculated features, the model prediction can be calculated in milliseconds. Accordingly, in this example embodiment, the method can be performed in real-time on portable devices to support fast and early prediction of blood transfusion. The prediction score, has a simple interpretation, which can be converted into color representation (e.g. red, yellow, green warning) to allow a health provider to quickly grasp the prediction. This work supports the efforts of trauma care and Emergency Medical Services systems to forward-deploy instrumentation capable of hands-free documentation and early detection of the potential use of blood products.

In an example embodiment, the data processing system 104 may be configured to filter the collected first data based on a PPG signal quality index (PPG-SQI). The SQI is used to identify segments of the PPG waveform when there was agreement between a pulse oximeter monitor pulse rate reading ($PR_1$) and an automated PPG measurement of peak-to-peak distance ($PR_2$).

If $$\frac{PR_1 - PR_2}{0.5 * (PR_1 + PR_2)} > 5\%,$$

then the segment of the PPG waveform is excluded from the first data set by the data processing system 104.

3. Hardware Overview

Figure 9:
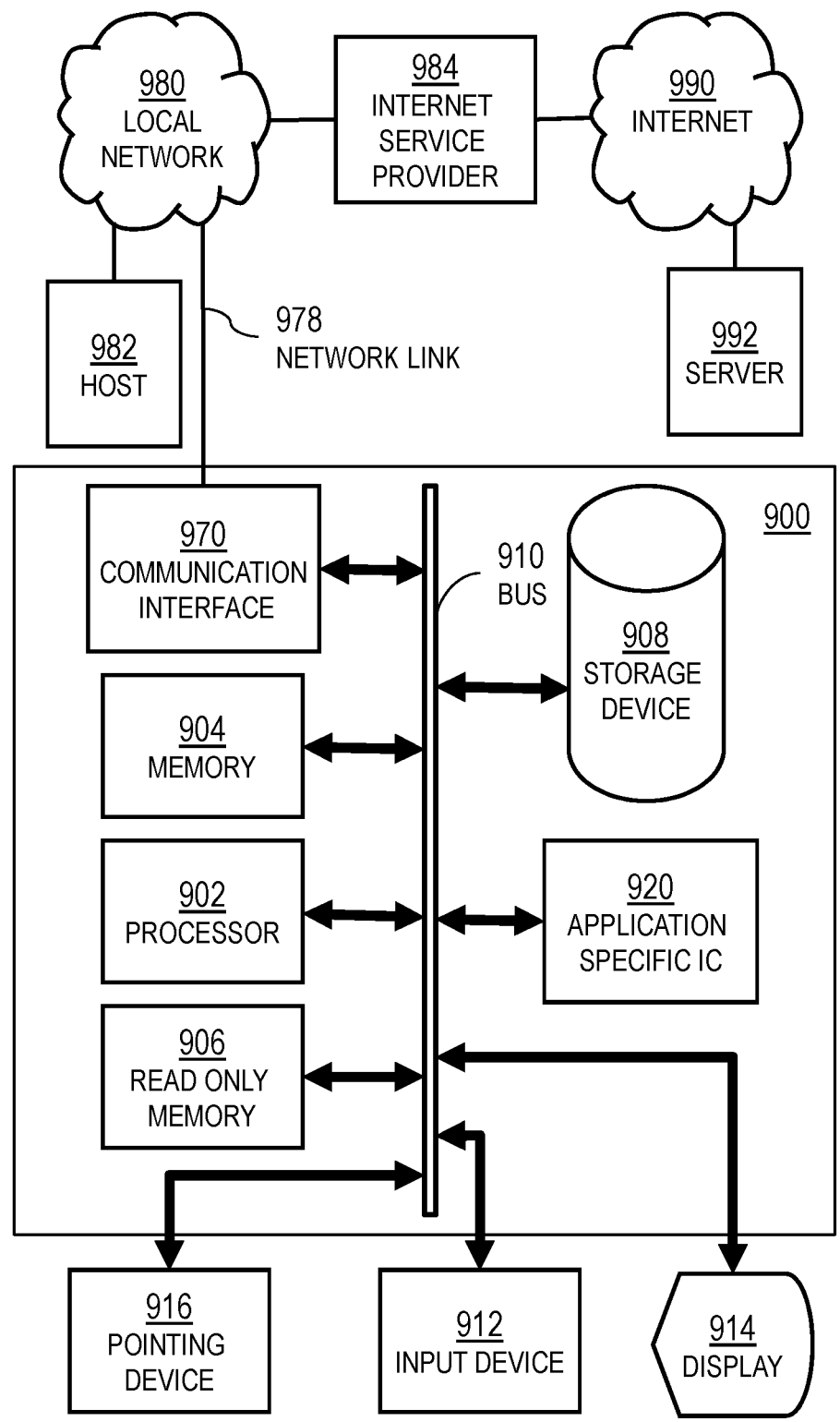
FIG. 9 is a block diagram that illustrates a computer system upon which an embodiment of the invention may be implemented.

FIG. 9 is a block diagram that illustrates a computer system 900 upon which an embodiment of the invention may be implemented. Computer system 900 includes a communication mechanism such as a bus 910 for passing information between other internal and external components of the computer system 900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 900, or a portion thereof, constitutes a means for performing one or more steps of one or more methods described herein.

A sequence of binary digits constitutes digital data that is used to represent a number or code for a character. A bus 910 includes many parallel conductors of information so that information is transferred quickly among devices coupled to the bus 910. One or more processors 902 for processing information are coupled with the bus 910. A processor 902 performs a set of operations on information. The set of operations include bringing information in from the bus 910 and placing information on the bus 910. The set of operations also typically include comparing two or more units of information, shifting positions of units of information, and combining two or more units of information, such as by addition or multiplication. A sequence of operations to be executed by the processor 902 constitutes computer instructions.

Computer system 900 also includes a memory 904 coupled to bus 910. The memory 904, such as a random access memory (RAM) or other dynamic storage device, stores information including computer instructions. Dynamic memory allows information stored therein to be changed by the computer system 900. RAM allows a unit of information stored at a location called a memory address to be stored and retrieved independently of information at neighboring addresses. The memory 904 is also used by the processor 902 to store temporary values during execution of computer instructions. The computer system 900 also includes a read only memory (ROM) 906 or other static storage device coupled to the bus 910 for storing static information, including instructions, that is not changed by the computer system 900. Also coupled to bus 910 is a non-volatile (persistent) storage device 908, such as a magnetic disk or optical disk, for storing information, including instructions, that persists even when the computer system 900 is turned off or otherwise loses power.

Information, including instructions, is provided to the bus 910 for use by the processor from an external input device 912, such as a keyboard containing alphanumeric keys operated by a human user, or a sensor. A sensor detects conditions in its vicinity and transforms those detections into signals compatible with the signals used to represent information in computer system 900. Other external devices coupled to bus 910, used primarily for interacting with humans, include a display device 914, such as a cathode ray tube (CRT) or a liquid crystal display (LCD), for presenting images, and a pointing device 916, such as a mouse or a trackball or cursor direction keys, for controlling a position of a small cursor image presented on the display 914 and issuing commands associated with graphical elements presented on the display 914.

In the illustrated embodiment, special purpose hardware, such as an application specific integrated circuit (IC) 920, is coupled to bus 910. The special purpose hardware is configured to perform operations not performed by processor 902 quickly enough for special purposes. Examples of application specific ICs include graphics accelerator cards for generating images for display 914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 900 also includes one or more instances of a communications interface 970 coupled to bus 910. Communication interface 970 provides a two-way communication coupling to a variety of external devices that operate with their own processors, such as printers, scanners and external disks. In general the coupling is with a network link 978 that is connected to a local network 980 to which a variety of external devices with their own processors are connected. For example, communication interface 970 may be a parallel port or a serial port or a universal serial bus (USB) port on a personal computer. In some embodiments, communications interface 970 is an integrated services digital network (ISDN) card or a digital subscriber line (DSL) card or a telephone modem that provides an information communication connection to a corresponding type of telephone line. In some embodiments, a communication interface 970 is a cable modem that converts signals on bus 910 into signals for a communication connection over a coaxial cable or into optical signals for a communication connection over a fiber optic cable. As another example, communications interface 970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 970 sends and receives electrical, acoustic or electromagnetic signals, including infrared and optical signals that carry information streams, such as digital data.

The term computer-readable medium is used herein to refer to any medium that participates in providing information to processor 902, including instructions for execution. Such a medium may take many forms, including, but not limited to, non-volatile media, volatile media and transmission media. Non-volatile media include, for example, optical or magnetic disks, such as storage device 908. Volatile media include, for example, dynamic memory 904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 902, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 902, except for carrier waves and other signals.

Logic encoded in one or more tangible media includes one or both of processor instructions on a computer-readable storage media and special purpose hardware, such as ASIC 920.

Network link 978 typically provides information communication through one or more networks to other devices that use or process the information. For example, network link 978 may provide a connection through local network 980 to a host computer 982 or to equipment 984 operated by an Internet Service Provider (ISP). ISP equipment 984 in turn provides data communication services through the public, world-wide packet-switching communication network of networks now commonly referred to as the Internet 990. A computer called a server 992 connected to the Internet provides a service in response to information received over the Internet. For example, server 992 provides information representing video data for presentation at display 914.

The invention is related to the use of computer system 900 for implementing the techniques described herein. According to one embodiment of the invention, those techniques are performed by computer system 900 in response to processor 902 executing one or more sequences of one or more instructions contained in memory 904. Such instructions, also called software and program code, may be read into memory 904 from another computer-readable medium such as storage device 908. Execution of the sequences of instructions contained in memory 904 causes processor 902 to perform the method steps described herein. In alternative embodiments, hardware, such as application specific integrated circuit 920, may be used in place of or in combination with software to implement the invention. Thus, embodiments of the invention are not limited to any specific combination of hardware and software.

The signals transmitted over network link 978 and other networks through communications interface 970, carry information to and from computer system 900. Computer system 900 can send and receive information, including program code, through the networks 980, 990 among others, through network link 978 and communications interface 970. In an example using the Internet 990, a server 992 transmits program code for a particular application, requested by a message sent from computer 900, through Internet 990, ISP equipment 984, local network 980 and communications interface 970. The received code may be executed by processor 902 as it is received, or may be stored in storage device 908 or other non-volatile storage for later execution, or both. In this manner, computer system 900 may obtain application program code in the form of a signal on a carrier wave.

Various forms of computer readable media may be involved in carrying one or more sequence of instructions or data or both to processor 902 for execution. For example, instructions and data may initially be carried on a magnetic disk of a remote computer such as host 982. The remote computer loads the instructions and data into its dynamic memory and sends the instructions and data over a telephone line using a modem. A modem local to the computer system 900 receives the instructions and data on a telephone line and uses an infra-red transmitter to convert the instructions and data to a signal on an infra-red a carrier wave serving as the network link 978. An infrared detector serving as communications interface 970 receives the instructions and data carried in the infrared signal and places information representing the instructions and data onto bus 910. Bus 910 carries the information to memory 904 from which processor 902 retrieves and executes the instructions using some of the data sent with the instructions. The instructions and data received in memory 904 may optionally be stored on storage device 908, either before or after execution by the processor 902.

Figure 10:
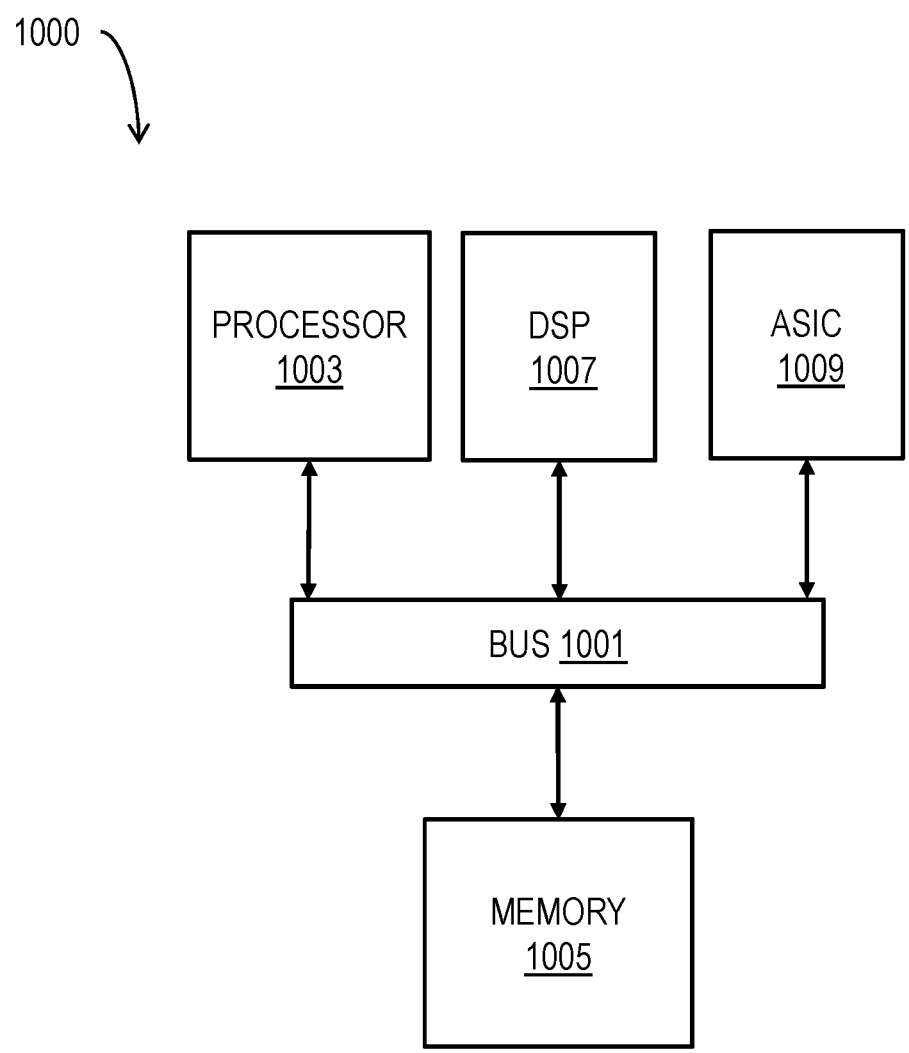
FIG. 10 is a block diagram that illustrates a chip set upon which an embodiment of the invention may be implemented.

FIG. 10 illustrates a chip set 1000 upon which an embodiment of the invention may be implemented. Chip set 1000 is programmed to perform one or more steps of a method described herein and includes, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1000, or a portion thereof, constitutes a means for performing one or more steps of a method described herein.

In one embodiment, the chip set 1000 includes a communication mechanism such as a bus 1001 for passing information among the components of the chip set 1000. A processor 1003 has connectivity to the bus 1001 to execute instructions and process information stored in, for example, a memory 1005. The processor 1003 may include one or more processing cores with each core configured to perform independently. A multi-core processor enables multiprocessing within a single physical package. Examples of a multi-core processor include two, four, eight, or greater numbers of processing cores. Alternatively or in addition, the processor 1003 may include one or more microprocessors configured in tandem via the bus 1001 to enable independent execution of instructions, pipelining, and multithreading. The processor 1003 may also be accompanied with one or more specialized components to perform certain processing functions and tasks such as one or more digital signal processors (DSP) 1007, or one or more application-specific integrated circuits (ASIC) 1009. A DSP 1007 typically is configured to process real-world signals (e.g., sound) in real time independently of the processor 1003. Similarly, an ASIC 1009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1003 and accompanying components have connectivity to the memory 1005 via the bus 1001. The memory 1005 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1005 also stores the data associated with or generated by the execution of one or more steps of the methods described herein.

4. Extensions, Modifications and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method comprising:
   obtaining, on a processor, first data that indicates values for one or more parameters of a characteristic of a peak of a Fourier transform of a continuous electrocardiogram (ECG) waveform collected during a treatment of a patient or both;
   applying, on the processor, coefficients to the values for the one or more parameters;
   determining, on the processor, second data that indicates a prediction that a caregiver will order a blood transfusion during the treatment based on applying the coefficients to the values for the one or more parameters; and
   presenting on a display device output data based on the second data.

2. The method of claim 1, wherein the first data further indicates values for one or more parameters of a characteristic of a peak of a Fourier transform of a continuous photoplethysmographic (PPG) waveform.

3. The method of claim 1, further comprising determining, on the processor, whether to order one or more blood units based on the prediction.

4. The method of claim 1, wherein the first data is collected over a fixed time interval, wherein the characteristic of the peak of the Fourier transform includes one or more of a frequency, an amplitude and a power;
   and wherein the parameters include one or more of a mean, a variance, a ratio of mean over median, a percentile and a Shannon entropy over the fixed time interval.

5. The method of claim 4, wherein the percentile comprises at least one of a 10 percentile, a 20 percentile, a 30 percentile, a 40 percentile, a 50 percentile, a 60 percentile, a 70 percentile, a 80 percentile, a 90 percentile and a 100 percentile of the characteristic of the peak over the fixed time interval.

6. The method of claim 4, wherein the prediction is based on a time range of at least one of up to 3 hours after the collection of the first data, up to 6 hours after the collection of the first data, and up to 12 hours after the collection of the first data.

7. The method of claim 1, wherein the first data indicates a threshold value for each of one or more parameters of the characteristic of a plurality of peaks of the Fourier transform of the ECG waveform.

8. The method of claim 1 further comprising obtaining, on the processor, third data that indicates values for one or more secondary parameters of a characteristic of the patient;
   wherein applying the coefficients to the one or more parameters further includes applying coefficients to the values for the one or more secondary parameters;
   and wherein the secondary parameters include one or more of an age and a gender of the patient.

9. The method of claim 1, further comprising determining, on the processor, values for the coefficients of the one or more parameters including:
   obtaining, on the processor, preliminary data for the one or more parameters of the characteristic of the peak of the Fourier transform of the ECG waveform during treatment of a plurality of patients or both;
   assigning, on the processor, a result for each patient based on whether the patient received a blood transfusion during the treatment;
   fitting, on the processor, the preliminary data to the results for the plurality of patients; and
   determining, on the processor, the coefficients for the one or more parameters, to determine a model for predicting whether a patient will require a blood transfusion based on the first data.

10. The method of claim 1, further comprising:
    applying, on the processor, secondary coefficients to the values of the one or more parameters; and determining, on the processor, fourth data that indicates a prediction that the caregiver will order a massive blood transfusion of at least five blood units during the treatment based on applying the secondary coefficients to the values for the one or more parameters.

11. The method of claim 10, wherein the prediction is based on a time range of at least 3 hours after the collection of the first data.

12. The method of claim 10, wherein the prediction is based on the massive blood transfusion of at least ten blood units and a time range of at least one of 10 hours and 24 hours after the collection of the first data.

13. The method of claim 1, wherein values of the coefficients are revised based on clinical data for the one or more parameters of the characteristic of the peak of the Fourier transform of the ECG waveform during treatment of a plurality of patients or both.

14. A method comprising:
obtaining, on a processor, first data that indicates values for one or more parameters of a characteristic of a peak of a Fourier transform of at least one of a continuous photoplethysmographic (PPG) waveform or a continuous electrocardiogram (ECG) waveform collected during a treatment of a patient or both;
applying, on the processor, coefficients to the values for the one or more parameters;
determining, on the processor, second data that indicates a prediction that a caregiver will order a blood transfusion during the treatment based on applying the coefficients to the values for the one or more parameters; and
presenting on a display device output data based on the second data;
wherein the first data indicates threshold values for each of one or more parameters of the characteristic of four peaks of the Fourier transform of the PPG waveform that comprise respective frequency ranges of 0-1 Hz, 1-3 Hz, 3-4 Hz and 5-6 Hz over a fixed time interval.

15. A method comprising:
receiving, on a processor, at least one of a photoplethysmographic (PPG) waveform and a continuous electrocardiogram (ECG) waveform collected during a fixed time interval during a treatment of a patient;
performing, on the processor, a short-time Fourier transform (STFT) of the at least one of the PPG waveform and the ECG waveform over a time window that is less than the fixed time interval;
obtaining, on the processor, first data that indicates values for one or more parameters of a characteristic of a peak of the STFT of the at least one of the PPG waveform and the ECG waveform based on performing the STFT over a plurality of time windows that encompass the fixed time interval;
applying, on the processor, coefficients to the values for the one or more parameters;
determining, on the processor, second data that indicates a prediction that a caregiver will order a blood transfusion during the treatment based on applying the coefficients to the values for the one or more parameters; and
presenting on a display device output data based on the second data.

16. An apparatus comprising:
electrodes configured to measure a continuous electrocardiogram (ECG) waveform collected during a treatment of a patient;
a display device; and
at least one processor connected to the electrodes to receive the ECG waveform;
at least one memory including one or more sequence of instructions;
the at least one memory and the one or more sequence of instructions configured to, with the at least one processor, cause the apparatus to perform at least the following;
perform a Fourier transform of the ECG waveform;
obtain first data that indicates values for one or more parameters of a characteristic of a peak of the Fourier transform of the ECG waveform;
apply coefficients to the values for the one or more parameters,
determine second data that indicates a prediction for ordering a blood transfusion during the treatment based on applying the coefficients to the values for the one or more parameters; and
present on the display device output data based on the second data.

17. The apparatus of claim 16 wherein the at least one memory and the one or more sequence of instructions are further configured to, with the at least one processor, cause the apparatus to order one or more blood units, based on the prediction.

18. The apparatus of claim 16 wherein the at least one memory and the one or more sequence of instructions are further configured to, with the at least one processor, cause the apparatus to obtain the first data over a fixed time interval, wherein the characteristic of the peak of the Fourier transform includes one or more of a frequency, an amplitude and a power; and
wherein the parameters include one or more of a mean, a variance, a ratio of mean over median, a percentile and a Shannon entropy over the fixed time interval.

19. The apparatus of claim 16, wherein the prediction is based on a time range of at least one of up to 3 hours after the collection of the first data, up to 6 hours after the collection of the first data, and up to 12 hours after the collection of the first data.

20. A computer-readable medium carrying one or more sequences of instructions, wherein execution of the one or more sequences of instructions by one or more processors causes the one or more processors to perform the steps of:
applying coefficients to values for one or more parameters of a characteristic of a peak of a Fourier transform of a continuous electrocardiogram (ECG) waveform collected during a treatment of a patient; and determining a prediction that a caregiver will order a blood transfusion during the treatment based on applying the coefficients to the values for the one or more parameters; and
presenting on a display device output data based on the prediction.

21. An apparatus comprising:
a pulse oximeter configured to measure a continuous photoplethysmographic (PPG) waveform collected during a treatment of a patient;
electrodes configured to measure a continuous electrocardiogram (ECG) waveform collected during the treatment of the patient;
a display device; and
at least one processor connected to the pulse oximeter and the electrodes to receive at least one of the PPG waveform and ECG waveform;
at least one memory including one or more sequence of instructions;

the at least one memory and the one or more sequence of instructions configured to, with the at least one processor, cause the apparatus to perform at least the following;
   perform a Fourier transform of the at least one of the PPG waveform and the ECG waveform;
   obtain first data that indicates values for one or more parameters of a characteristic of a peak of the Fourier transform of the at least one of the PPG waveform and ECG waveform, wherein the first data indicates threshold values for each of one or more parameters of the characteristic of four peaks of the Fourier transform of the PPG waveform that comprise respective frequency ranges of 0-1 Hz, 1-3 Hz, 3-4 Hz and 5-6 Hz over a fixed time interval;
   apply coefficients to the values for the one or more parameters,
   determine second data that indicates a prediction for ordering a blood transfusion during the treatment based on applying the coefficients to the values for the one or more parameters; and
   present on the display device output data based on the second data.

22. The apparatus of claim 21 wherein the at least one memory and the one or more sequence of instructions are further configured to, with the at least one processor, cause the apparatus to order one or more blood units, based on the prediction.

23. The apparatus of claim 21 wherein the at least one memory and the one or more sequence of instructions are further configured to, with the at least one processor, cause the apparatus to obtain the first data over the fixed time interval, wherein the characteristic of the peak of the Fourier transform includes one or more of a frequency, an amplitude and a power; and
   wherein the parameters include one or more of a mean, a variance, a ratio of mean over median, a percentile and a Shannon entropy over the fixed time interval.

24. The apparatus of claim 21, wherein the prediction is based on a time range of at least one of up to 3 hours after the collection of the first data, up to 6 hours after the collection of the first data, and up to 12 hours after the collection of the first data.

25. An apparatus comprising:
   a pulse oximeter configured to measure a continuous photoplethysmographic (PPG) waveform collected during a treatment of a patient;
   electrodes configured to measure a continuous electrocardiogram (ECG) waveform collected during the treatment of the patient;
   a display device; and
   at least one processor connected to the pulse oximeter and the electrodes to receive at least one of the PPG waveform and ECG waveform;
   at least one memory including one or more sequence of instructions;
   the at least one memory and the one or more sequence of instructions configured to, with the at least one processor, cause the apparatus to perform at least the following;
     receive the at least one of the PPG waveform and the ECG waveform collected during a fixed time interval during the treatment of the patient;
     perform a short-time Fourier transform (STFT) of the at least one of the PPG waveform and the ECG waveform over a time window that is less than the fixed time interval;
     obtain first data that indicates values for one or more parameters of a characteristic of a peak of the STFT of the at least one of the PPG waveform and ECG waveform based on performing the STFT over a plurality of time windows that encompass the fixed time interval;
     apply coefficients to the values for the one or more parameters,
     determine second data that indicates a prediction for ordering a blood transfusion during the treatment based on applying the coefficients to the values for the one or more parameters; and
     present on the display device output data based on the second data.

26. The apparatus of claim 25 wherein the at least one memory and the one or more sequence of instructions are further configured to, with the at least one processor, cause the apparatus to order one or more blood units, based on the prediction.

27. The apparatus of claim 25 wherein the at least one memory and the one or more sequence of instructions are further configured to, with the at least one processor, cause the apparatus to obtain the first data over the fixed time interval, wherein the characteristic of the peak of the Fourier transform includes one or more of a frequency, an amplitude and a power; and
   wherein the parameters include one or more of a mean, a variance, a ratio of mean over median, a percentile and a Shannon entropy over the fixed time interval.

28. The apparatus of claim 25, wherein the prediction is based on a time range of at least one of up to 3 hours after the collection of the first data, up to 6 hours after the collection of the first data, and up to 12 hours after the collection of the first data.

* * * * *